US012667246B2

(12) United States Patent
Kofidis

(10) Patent No.: US 12,667,246 B2
(45) Date of Patent: Jun. 30, 2026

(54) LESS INVASIVE, FLEXIBLE RETRACTOR-CAMERA KIT FOR VIDEO ASSISTED ENDOSCOPIC SURGERY

(71) Applicants:NATIONAL UNIVERSITY OF SINGAPORE, Singapore (SG); NATIONAL UNIVERSITY HOSPITAL (SINGAPORE) PTE LTD, Singapore (SG)

(72) Inventor: Theodoros Kofidis, Singapore (SG)

( * ) Notice: Subject to any disclaimer, the term of this patent is extended or adjusted under 35 U.S.C. 154(b) by 526 days.

(21) Appl. No.: 18/026,349

(22) PCT Filed: Sep. 15, 2021

(86) PCT No.: PCT/SG2021/050558
§ 371 (c)(1),
(2) Date: Mar. 24, 2023

(87) PCT Pub. No.: WO2022/060295
PCT Pub. Date: Mar. 24, 2022

(65) Prior Publication Data
US 2023/0371796 A1      Nov. 23, 2023

(30) Foreign Application Priority Data

Sep. 15, 2020    (SG) ............................ 10202009027Y

(51) Int. Cl.
| | |
|---|---|
| *A61B 1/00* | (2006.01) |
| *A61B 1/06* | (2006.01) |
| *A61B 1/313* | (2006.01) |
| *A61B 17/00* | (2006.01) |
| *A61B 17/02* | (2006.01) |

(52) U.S. Cl.
CPC ............ *A61B 1/00148* (2022.02); *A61B 1/06* (2013.01); *A61B 1/313* (2013.01); *A61B 17/0218* (2013.01); *A61B 2017/00783* (2013.01); *A61B 2017/00876* (2013.01)

(58) Field of Classification Search
CPC ....... A61B 1/00148; A61B 1/06; A61B 1/313; A61B 17/0218
See application file for complete search history.

(56) References Cited

U.S. PATENT DOCUMENTS

| | | | |
|---|---|---|---|
| 2002/0049367 A1* | 4/2002 | Irion ................ | A61B 17/00234 600/173 |
| 2007/0129608 A1 | 6/2007 | Sandhu | |
| 2008/0108877 A1 | 5/2008 | Bayat | |
| 2012/0035638 A1 | 2/2012 | Mathaneswaran et al. | |
| 2015/0282795 A1 | 10/2015 | Schabert et al. | |
| 2018/0055502 A1 | 3/2018 | Charles et al. | |

FOREIGN PATENT DOCUMENTS

| | | |
|---|---|---|
| WO | 2011072104 A1 | 6/2011 |
| WO | 2015042483 A2 | 3/2015 |

* cited by examiner

*Primary Examiner* — Aaron B Fairchild
(74) *Attorney, Agent, or Firm* — SOROKER AGMON NORDMAN

(57) ABSTRACT

A retractor-camera kit for minimally invasive surgery is provided. The kit includes a retractor comprising at least a top blade and a first side blade connected to one another through a hinge, a handle connected to the retractor, and a camera connected to the retractor via a designated holder to provide visualization of a surgical site while avoiding the need for an additional incision for passing an imaging unit therethrough.

23 Claims, 15 Drawing Sheets

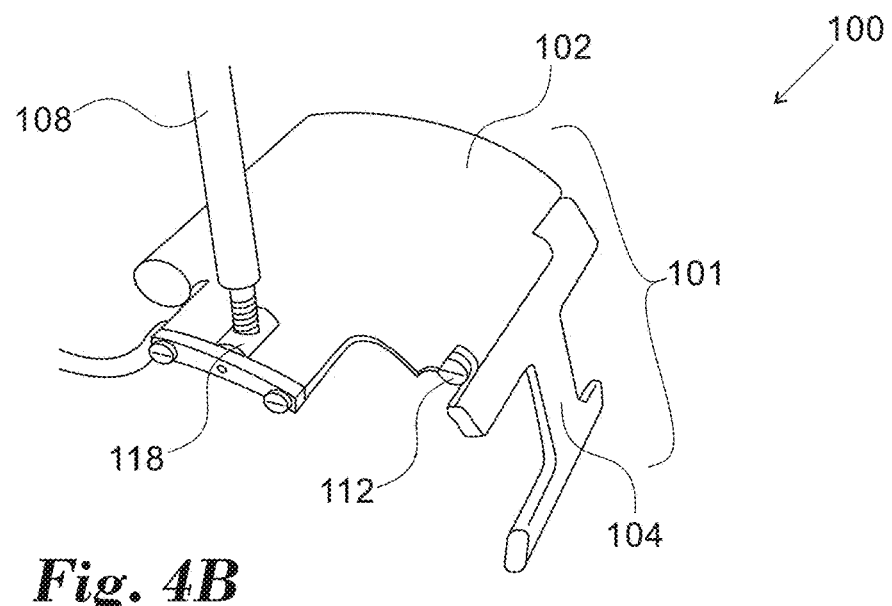
*Fig. 4B*
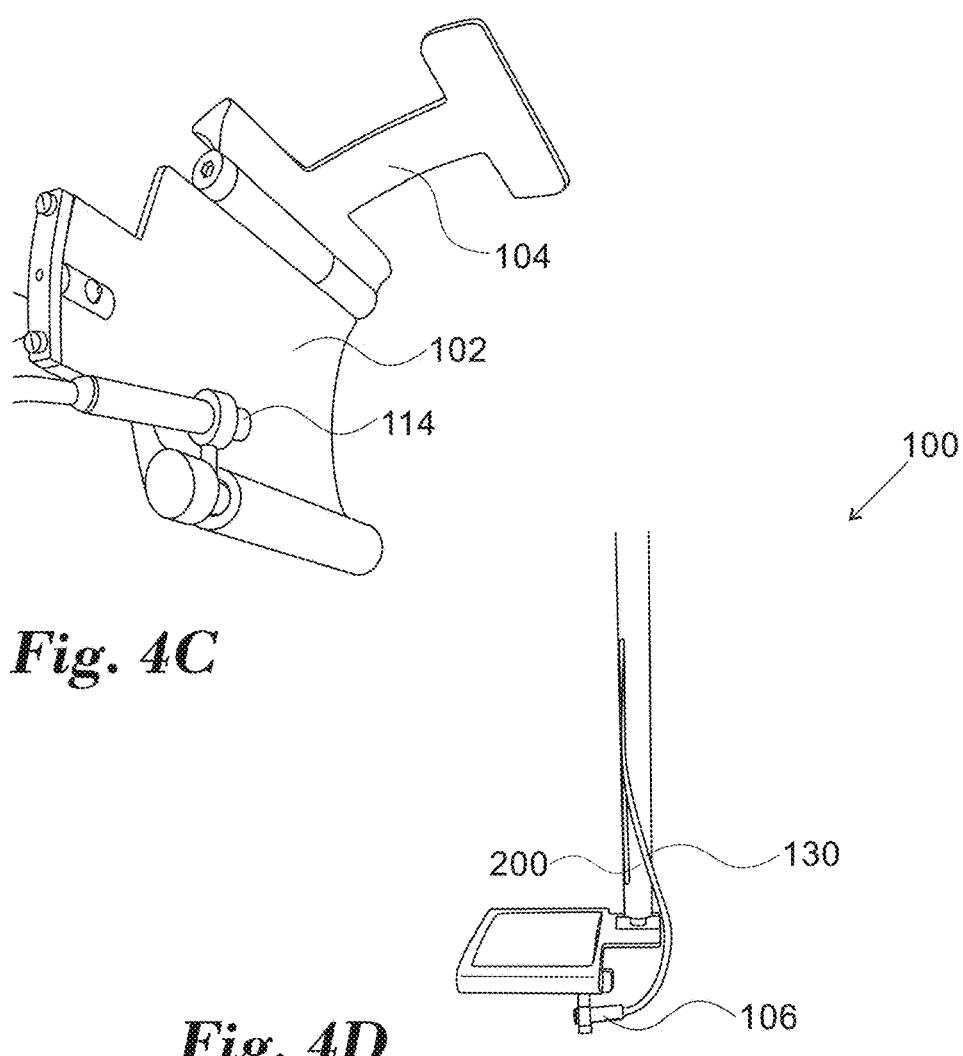
*Fig. 4C*
*Fig. 4D*

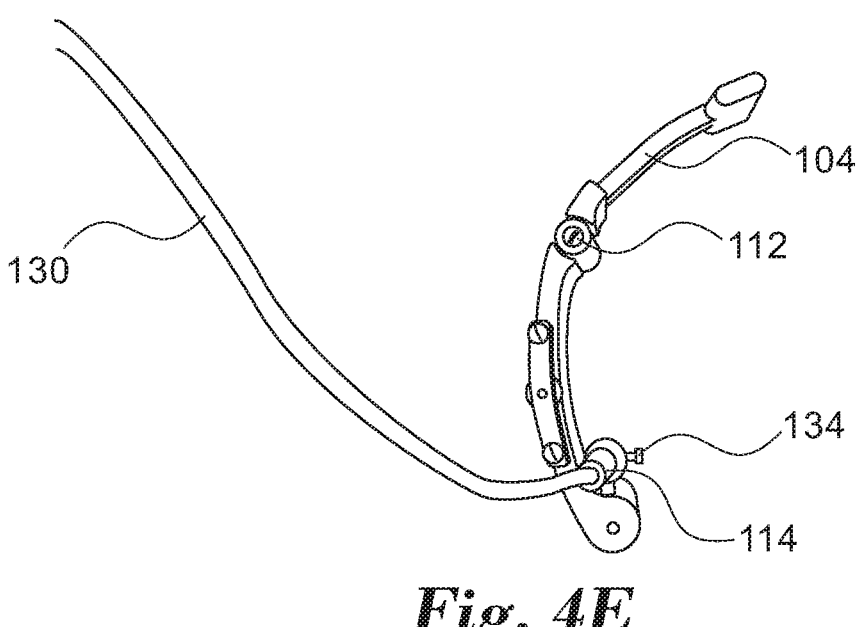
*Fig. 4E*
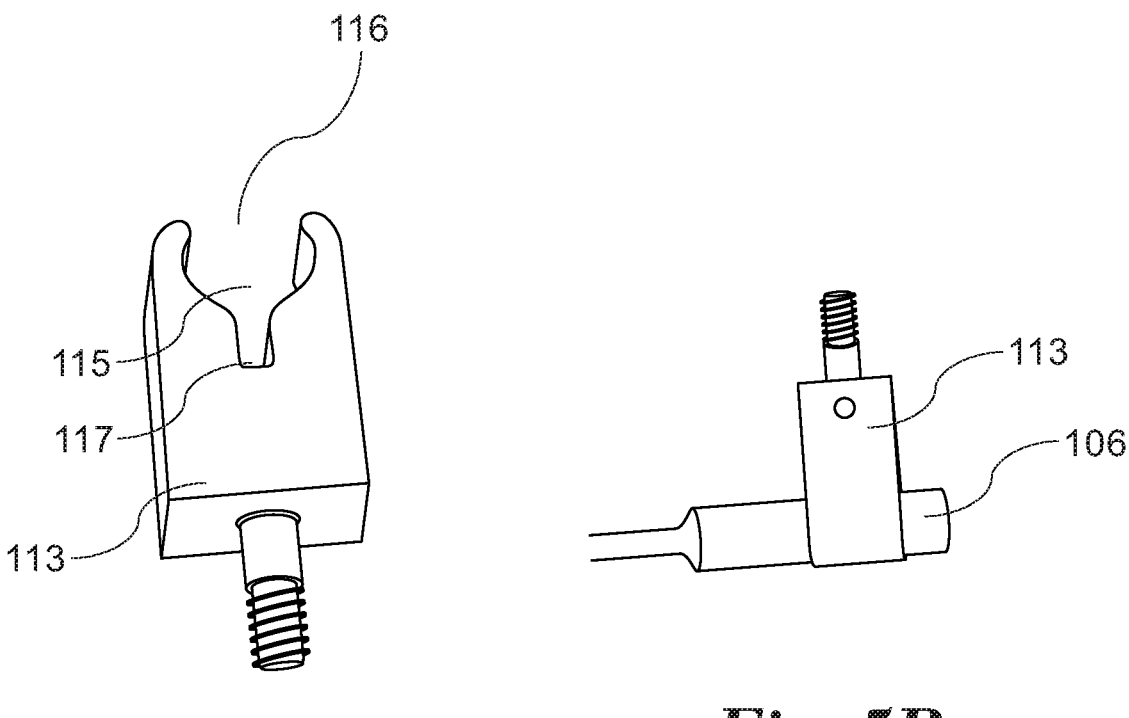
*Fig. 5A*                    *Fig. 5B*

104b

104c

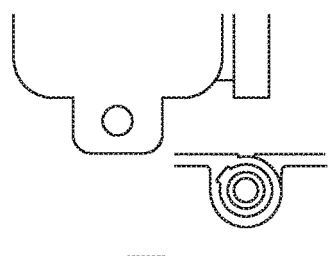
*Fig. 9*
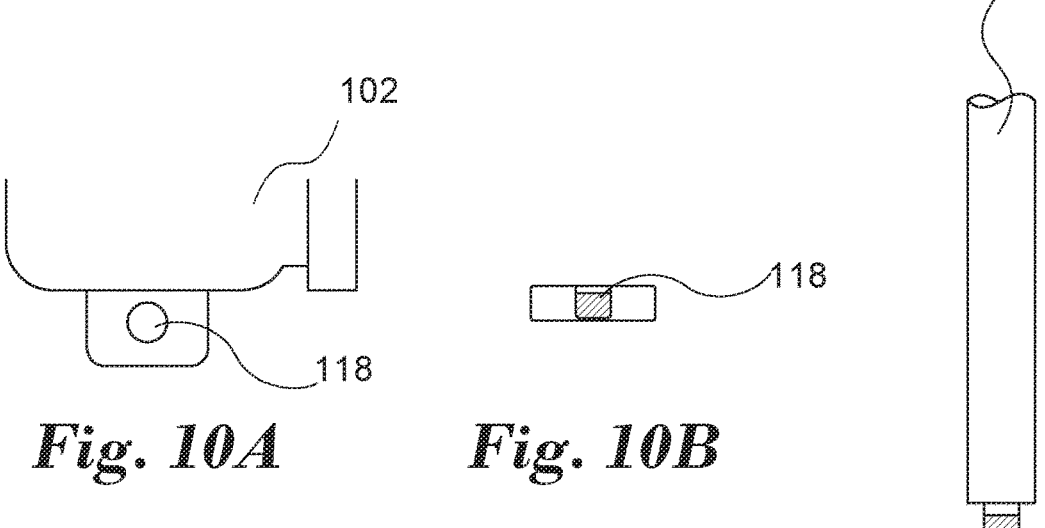
102
118
*Fig. 10A*
118
*Fig. 10B*
108
*Fig. 10C*
108
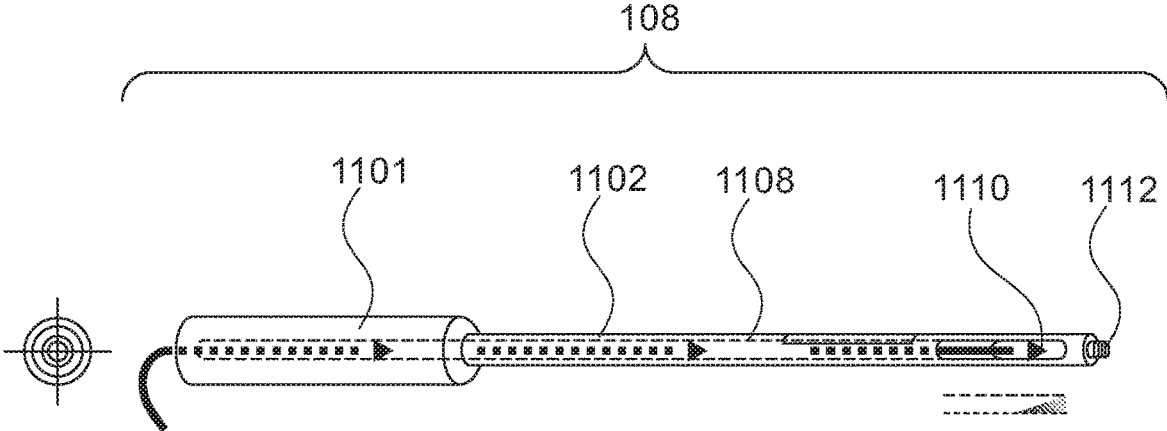
1101          1102          1108          1110          1112
*Fig. 11*

1214

1216

106

θ

1318

1320(1)

1320(2)

1316

β

106

1314

1320(3)

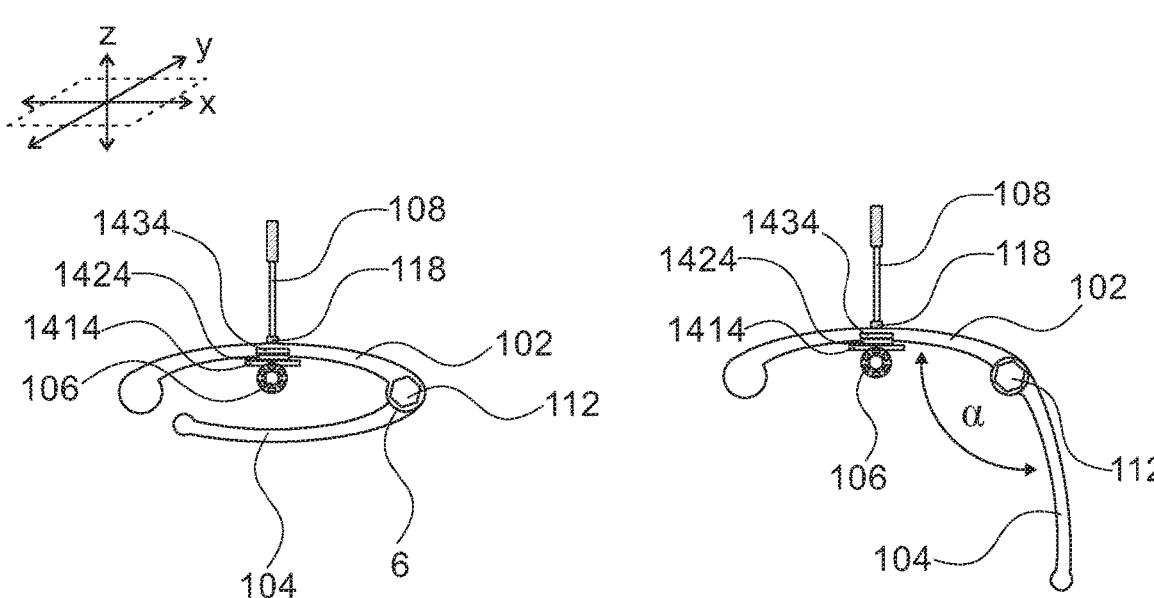
*Fig. 14A*        *Fig. 14B*
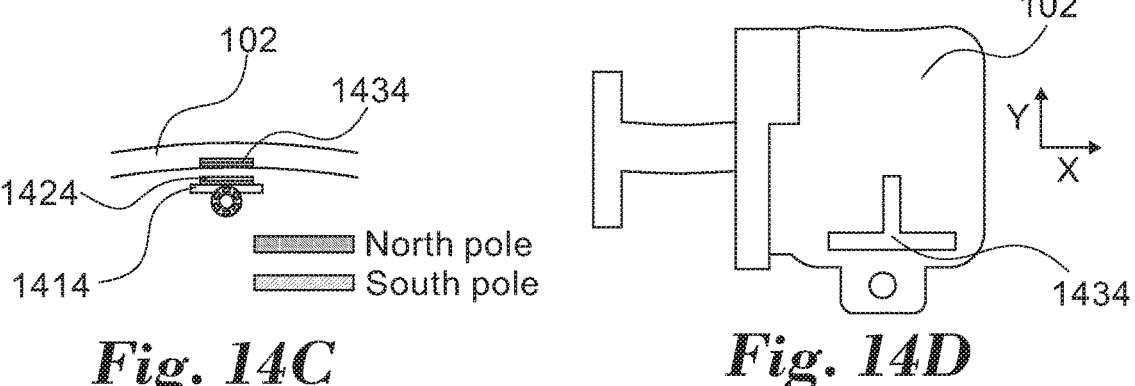
*Fig. 14C*        *Fig. 14D*
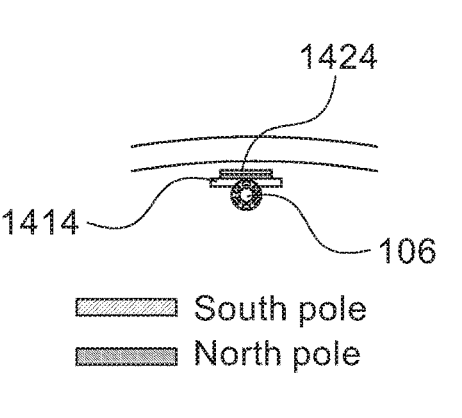
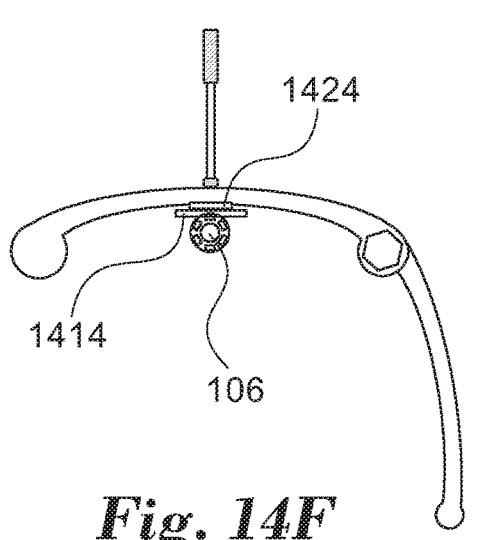
*Fig. 14E*        *Fig. 14F*

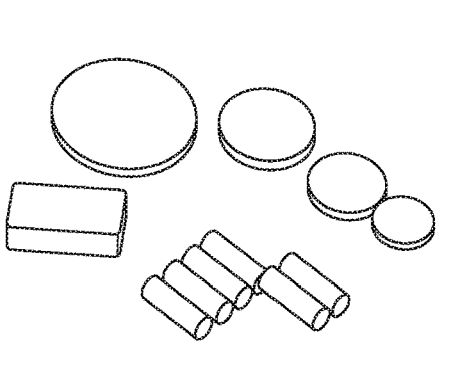
Fig. 15A
Fig. 15B
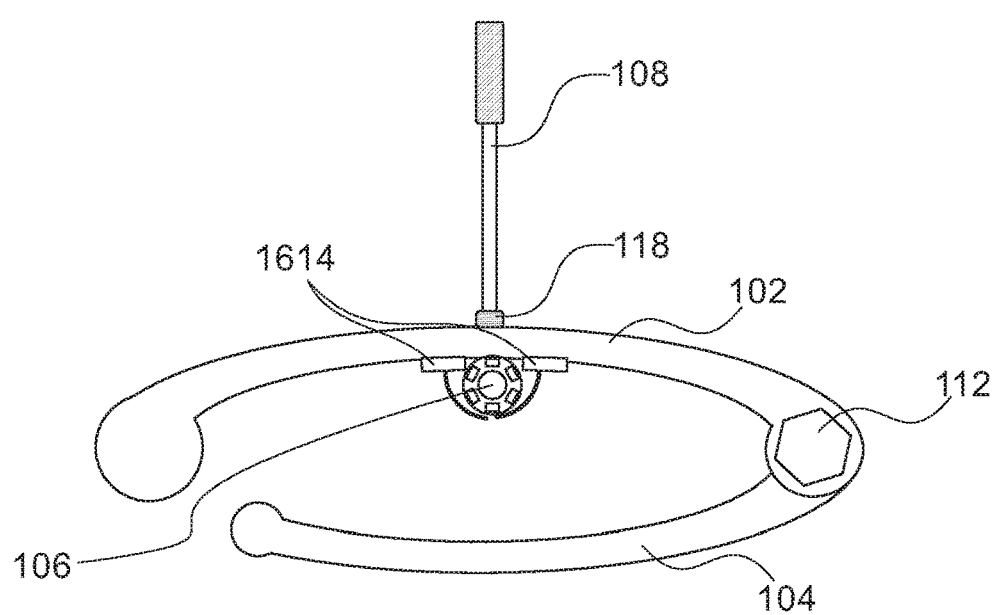
Fig. 16A
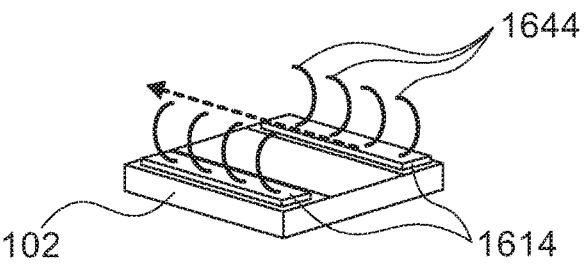
Fig. 16B

LESS INVASIVE, FLEXIBLE RETRACTOR-CAMERA KIT FOR VIDEO ASSISTED ENDOSCOPIC SURGERY

TECHNICAL FIELD

The present disclosure generally relates to surgical aiding devices, and more specifically to a less invasive, flexible retractor-camera kit for video assisted endoscopic surgery such as minimally invasive mitral valve surgery (MiMVS) through right mini-thoracotomy (RT).

BACKGROUND

Minimally invasive surgery has become routine for various types of surgeries, for example, mitral valve repair and replacement, due to the decrease in surgical trauma and accelerated postoperative recovery compared to open heart mitral valve surgery. For a successful minimally invasive surgery, optimal exposure and visualization of the mitral valve is of high importance.

Currently, soft-tissue retractor and atrium lift retractor (also called atrial retractor) are used to expose the working field at the procedure incision and a small endoscopic camera is introduced into a patient's chest through another incision port to serve as an important assistant viewing tool for the surgeon and the surgical team. However, performing an additional incision in the chest of a patient for insertion of a camera therethrough incurs several problems, among them the additional incision itself, which causes additional trauma to the patient, requiring an additional surgical staff member to manually hold the shaft or trocar of the endoscopic camera and the difficulty in maneuvering and continuously adjusting the location of the camera in order to obtain various viewing angles of the target structure being operated.

There is thus a need for a system that can overcome the disadvantages of current endoscopic surgery systems and procedures.

SUMMARY

According to an aspect of some embodiments of the present disclosure, there is provided a system for assisting with mitral exposure during minimally invasive mitral valve surgery (MiMVS) through right mini-thoracotomy (RT) and for acquiring images or video in real-time during such surgery.

According to some embodiments of the disclosure, there is provided an atrium lift retractor integrated with a miniature-video camera, which eliminates the need for an additional chest penetration or incision, frees up space in the operation field since the camera is inserted with the retractor from the same incision and there is no need for an additional staff member to navigate the camera separately from the retractor, reduces bleeding and heart injury risk by avoiding the need for an additional incision, provides better cosmetics and faster healing and allows for better and more flexible handling of the camera and retractor. Accordingly, complex procedures may be facilitated, while existing procedures may be carried out safer and faster.

Moreover, current retraction-imaging apparatuses demand time and energy and are bulky and rigid compared to the integrated camera retractor of the present disclosure, which comprises a miniaturized camera that requires less energy and is easy to maneuver due to its small size and flexibility. Flexibility of the integrated camera retractor may be reflected in that the miniaturized camera may be inserted into the chest of a patient such to be positioned in various positions. In addition, once the miniaturized camera is attached onto the retractor blade comprising an articulating joint, the camera may be moved in various angles to provide various viewing angles of the area of interest, i.e., the mitral valve.

In some embodiments, an atrium lift retractor with an integrated endoscopic micro-camera is disclosed. This surgical kit comprises a miniature-video camera that may replace the current bulky endoscopic camera, and an atrium lift retractor with a camera holding structure. The atrium lift retractor may have a single blade or multiple blades and may be supported and controlled by a shaft holder. The atrium lift retractor may integrate with a holding structure to fit with the miniature-video camera. In heart surgery, for example, minimally-invasive mitral valve surgery (MiMVS) through right mini-thoracotomy (RT), besides the incision or port where the procedure is being carried out and through which the atrium lift retractor may be inserted, there is often an additional incision port through the chest for introducing a video camera to serve as an important assistant tool for the surgeon and for the surgical team. The retractor-camera kit of the present disclosure eliminates the necessity of the additional incision, which reduces patient trauma and simultaneously provides clear and unobstructed access to the surgery area by comprising a miniature-video camera integrated with the retractor, both of which enter as a single unit through the same entry of the working incision into the target organ.

According to some embodiments of the disclosure, there is provided a retractor-camera kit for minimally invasive heart surgery. The retractor-camera kit may comprise a retractor comprising at least a top blade and a first side blade connected to one another through a hinge, a handle configured to be connected to the retractor, a camera for acquiring images, and a holder onto which the camera is connected and thereby held by the retractor to provide visualization of a surgical site.

Optionally, the handle may comprise a hollow shaft through which the camera passes.

Optionally, the handle may comprise an opening at a proximal end of the handle for the camera to exit through and reach the holder.

In some embodiments, the holder may be configured to enable maneuverability of the camera while still attached to the holder for directing the camera to different directions and for adjusting, magnification and field of view of the camera.

In some embodiments, the holder may be attached to the retractor via magnetic attraction.

Optionally, each of the holder and the retractor may comprise a magnet thereby connecting the holder to the retractor via magnetic attraction.

In some embodiments, the holder may be attached to the retractor via a slide-and-lock mechanism.

In some embodiments, the holder may be fixed to an upper left corner of the top blade via a swivel ball joint to provide said maneuverability.

In some embodiments, the holder may comprise a hole to hold the camera.

Optionally, the hole may be shaped as an unenclosed circle.

Optionally, the hole may be shaped as a major segment of a circle.

In some embodiments, the holder may comprise a split ring with an opening to hold the camera.

Optionally, the at least top blade and first side blade may be configured to switch between a closed state and an open state, wherein during said closed state the at least top blade and first side blade are folded such to occupy little space for ease of insertion into the surgical site, and during said open state the at least top blade and side blade distance from one another to create an angle therebetween of 0 to 180 degrees, for expanding and distancing tissue walls away from the camera to provide visualization of the surgical site during a surgical procedure.

In some embodiments, the at least top blade and at least first side blade may be solid plates.

Optionally, the solid plate at least first side blade may further comprise an opening at a bottom end of the at least first side blade.

In some embodiments, the at least top blade may comprise a solid plate and the at least first side blade may be a laid sideways "T"-shaped plate.

In some embodiments, the length of the laid sideways "T"-shaped blade may be between two thirds, up to a full length of the solid plate at least top blade.

Optionally, the laid sideways "T"-shaped first side blade may be located at a center of the solid plate at least top blade.

In some embodiments, the at least top blade may comprise a solid plate and the at least first side blade may be a "H"-shaped plate.

Optionally, the retractor may further comprise a second side blade attached to the top blade on a side opposite the side where the first side blade is attached to the top blade.

Optionally, the retractor may further comprise a flexible blade configured to be attached on one of its ends to the first side blade and on another of its ends to the second side blade, to create a semi-circle shaped retractor for expanding and distancing tissue walls away from the camera in a substantially circular shape.

In some embodiments, the retractor-camera kit may further comprise at least one illumination source for illuminating the surgical site.

Optionally, the at least one illumination source may be a light panel incorporated within the top blade.

Optionally, the at least one illumination source may be a bulb or lamp incorporated along the hinge of the retractor.

BRIEF DESCRIPTION OF THE DRAWINGS

Some non-limiting exemplary embodiments or features of the disclosed subject matter are illustrated in the following drawings.

In the drawings.

4

Figure 3:
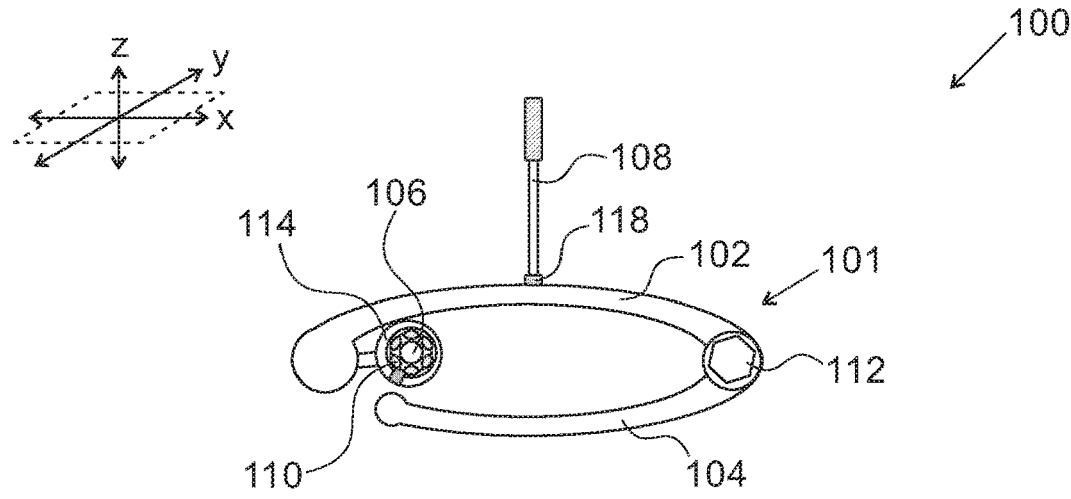
FIG. 3 is a schematic illustration of a front view of a two-blade atrium lift retractor in "closed" position integrated with a camera and a holding structure located at the right edge of the top blade, in accordance with embodiments of the present disclosure.
Figure 6A:
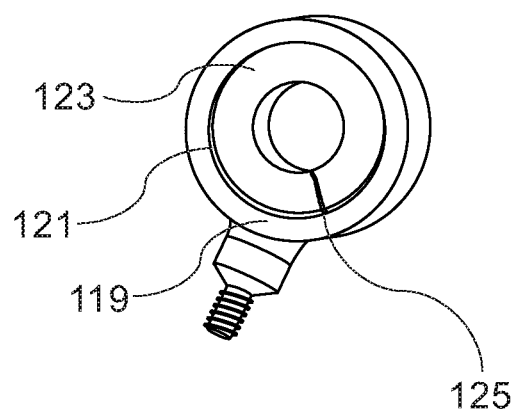
Figure 6B:
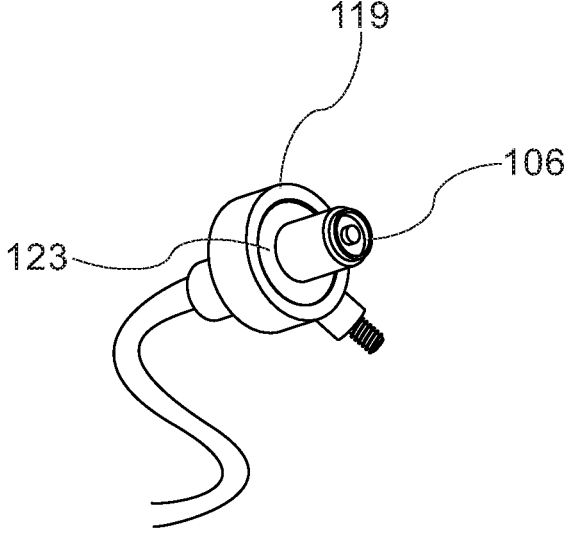
Figure 7:
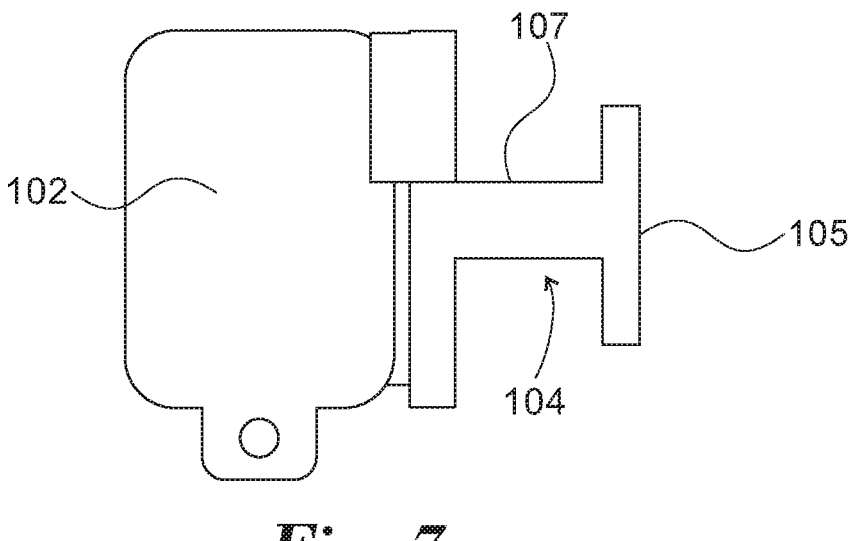
Figure 8A:
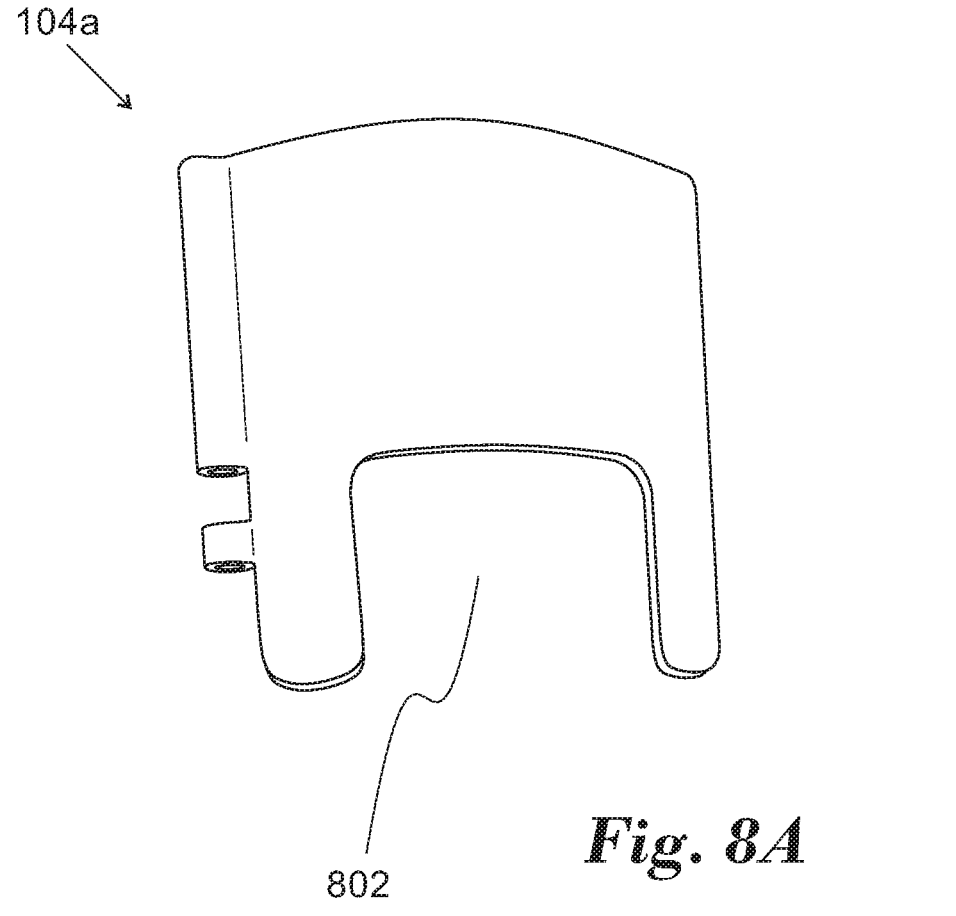
Figure 8B:
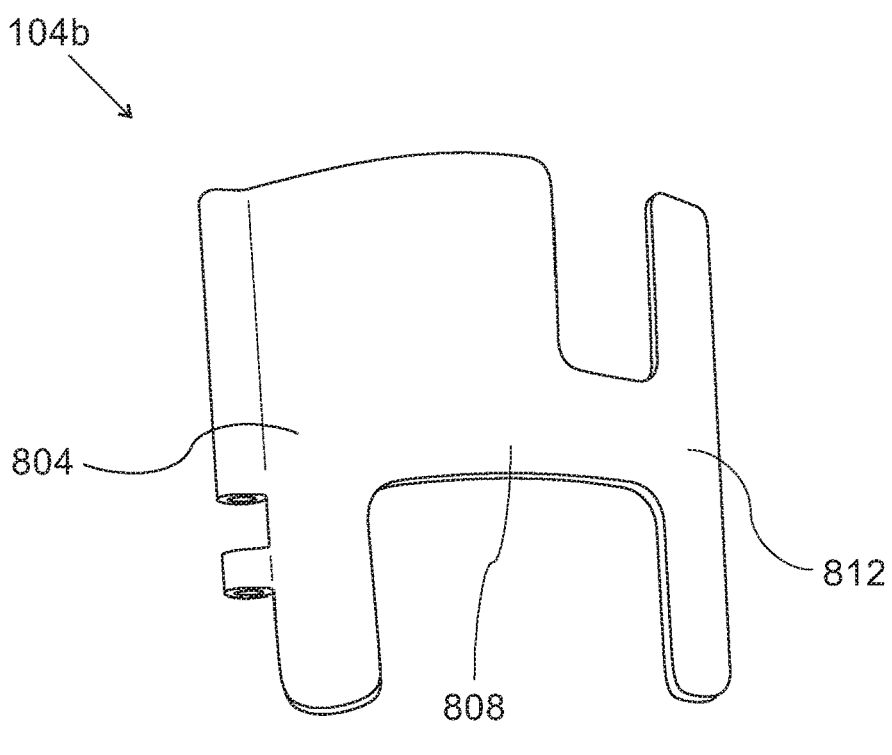
Figure 8C:
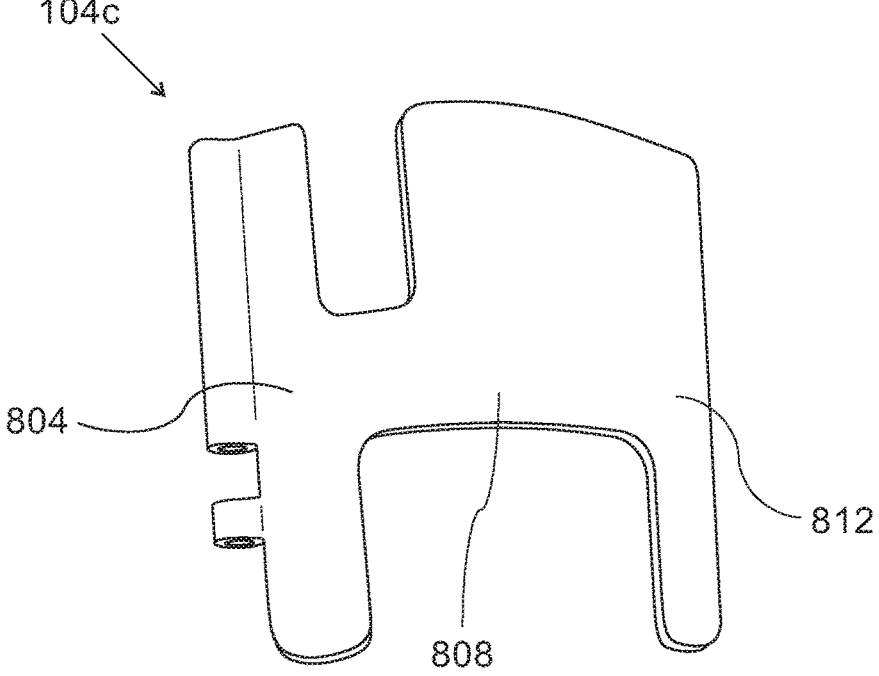
Figure 12A:
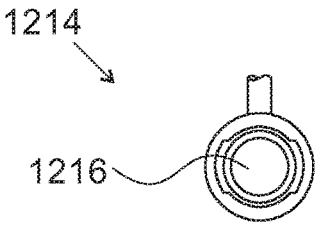
Figure 12B:
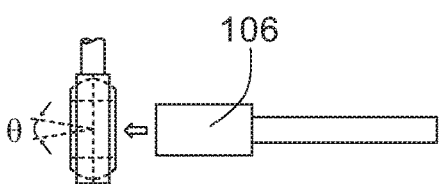
Figure 13A:
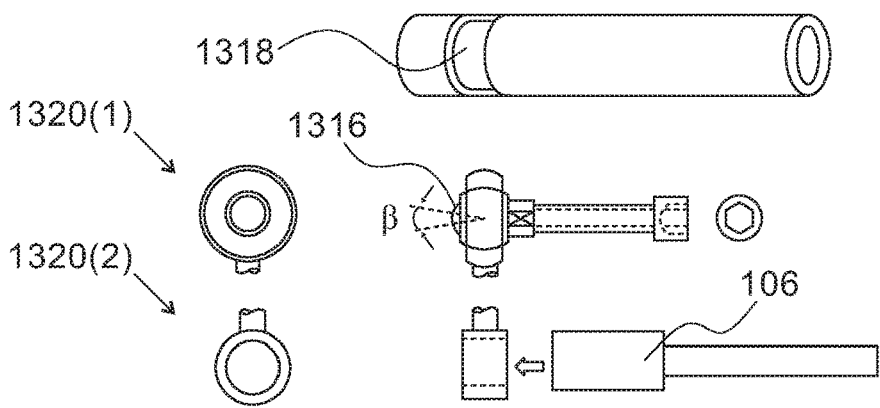
Figure 13B:
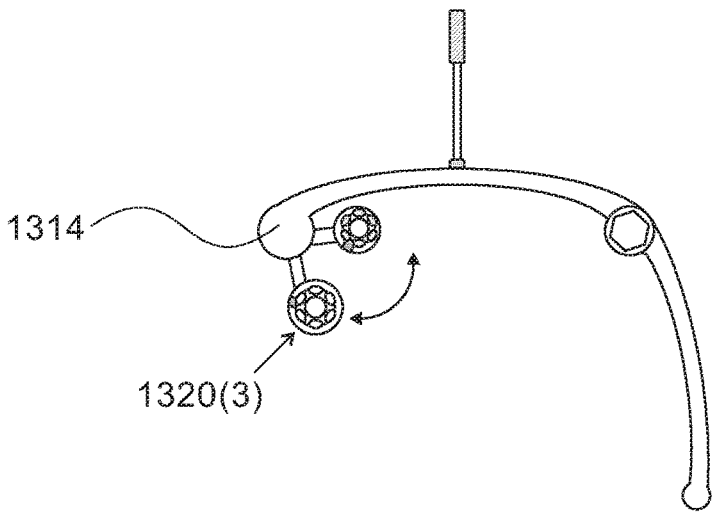
Figure 17A:
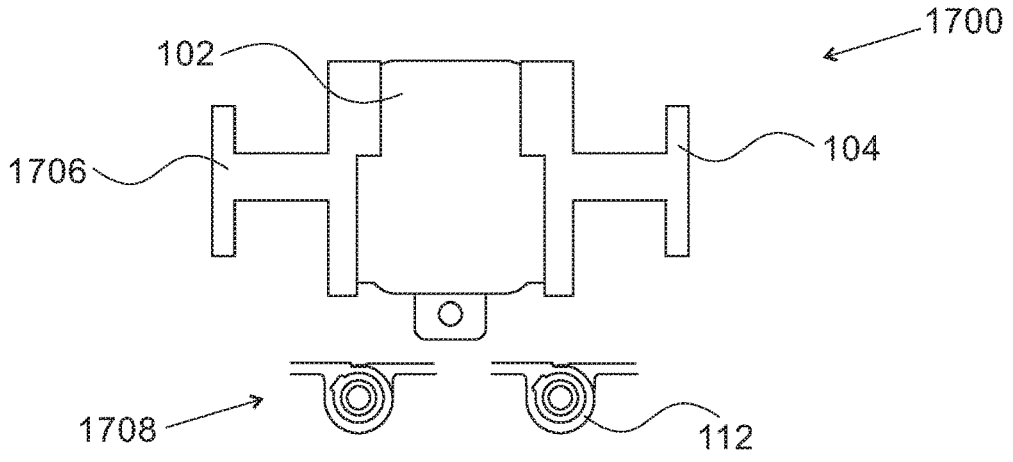
Figure 17B:
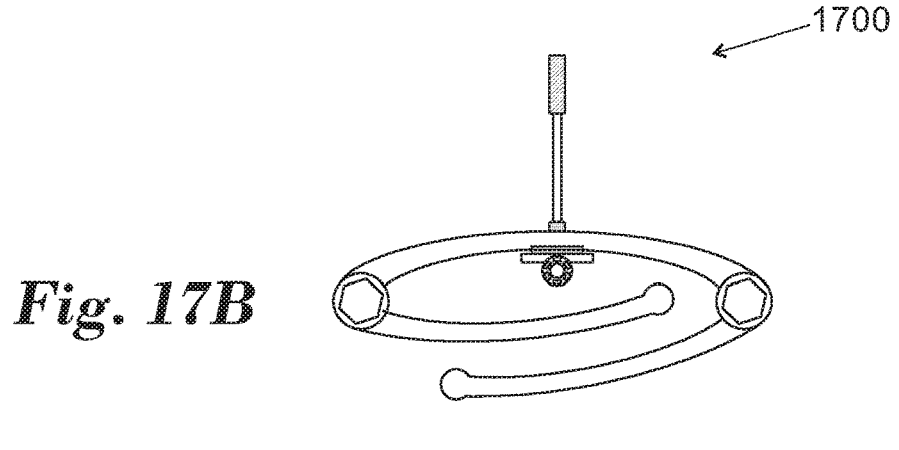
Figure 17C:
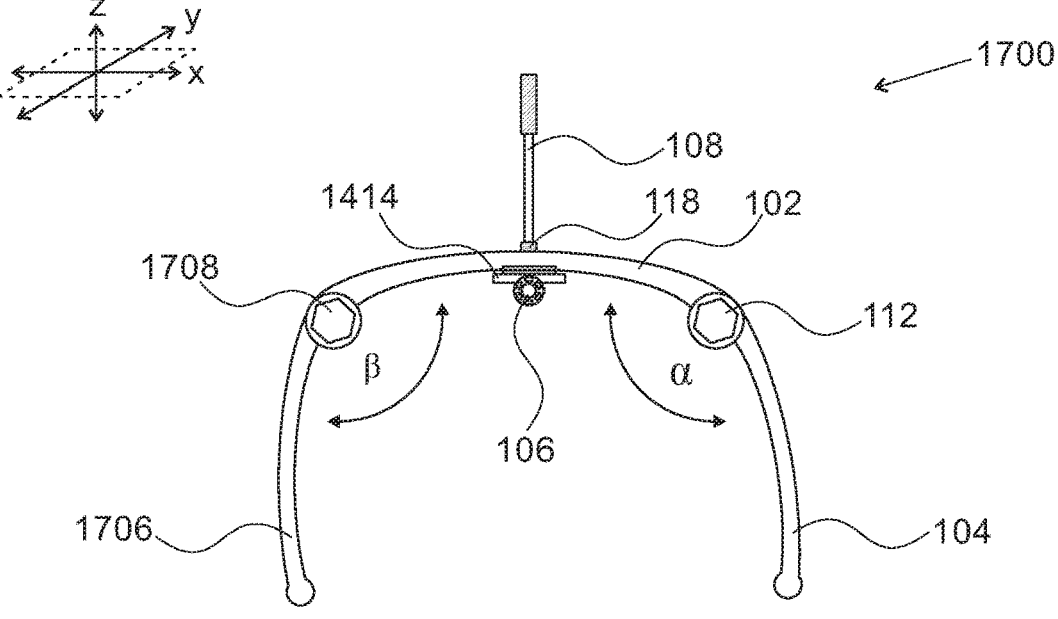
Figure 18:
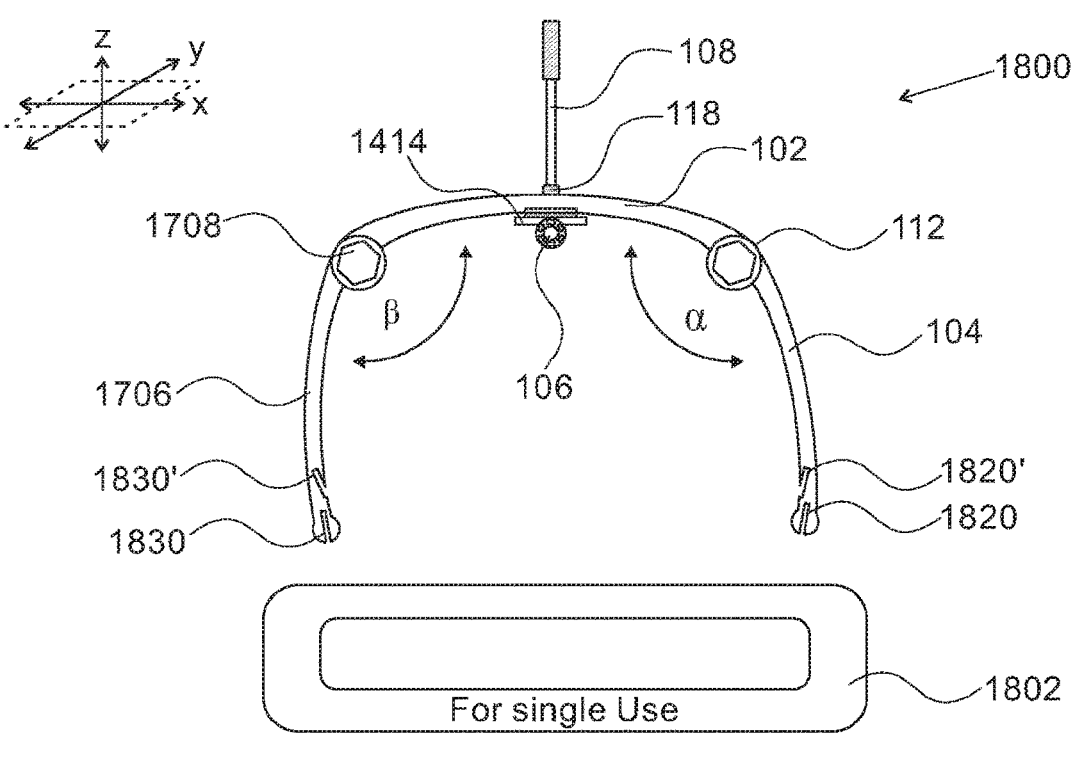
Figure 19:
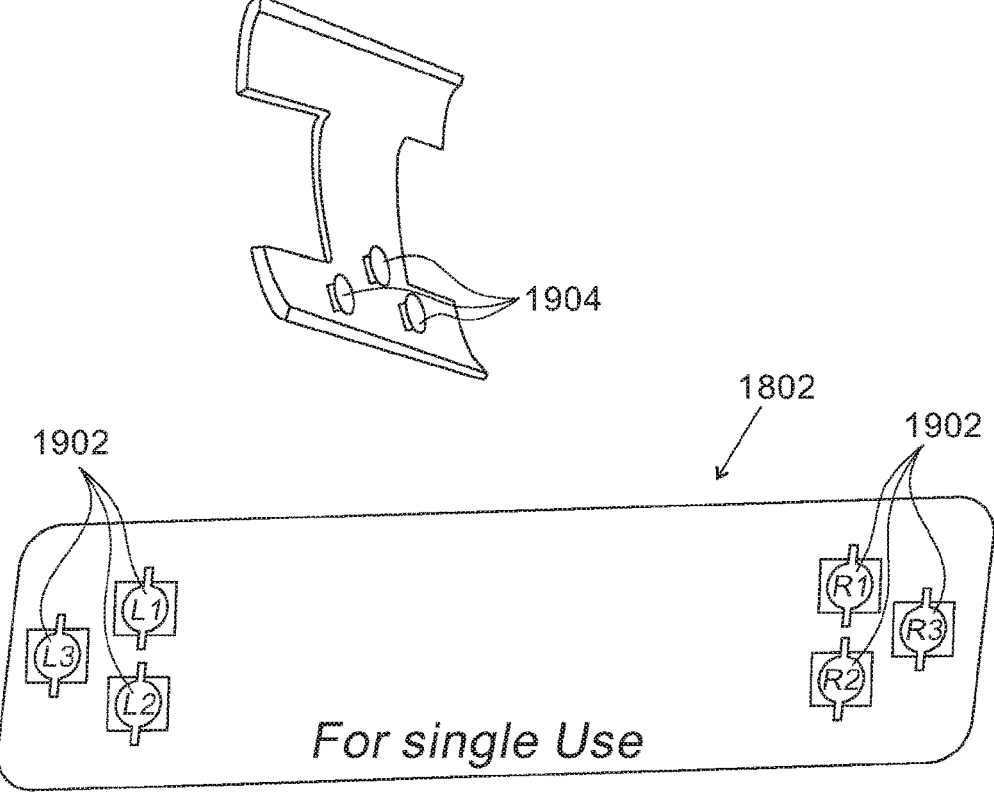
Figures 20A, 20B, 21A, 21B:
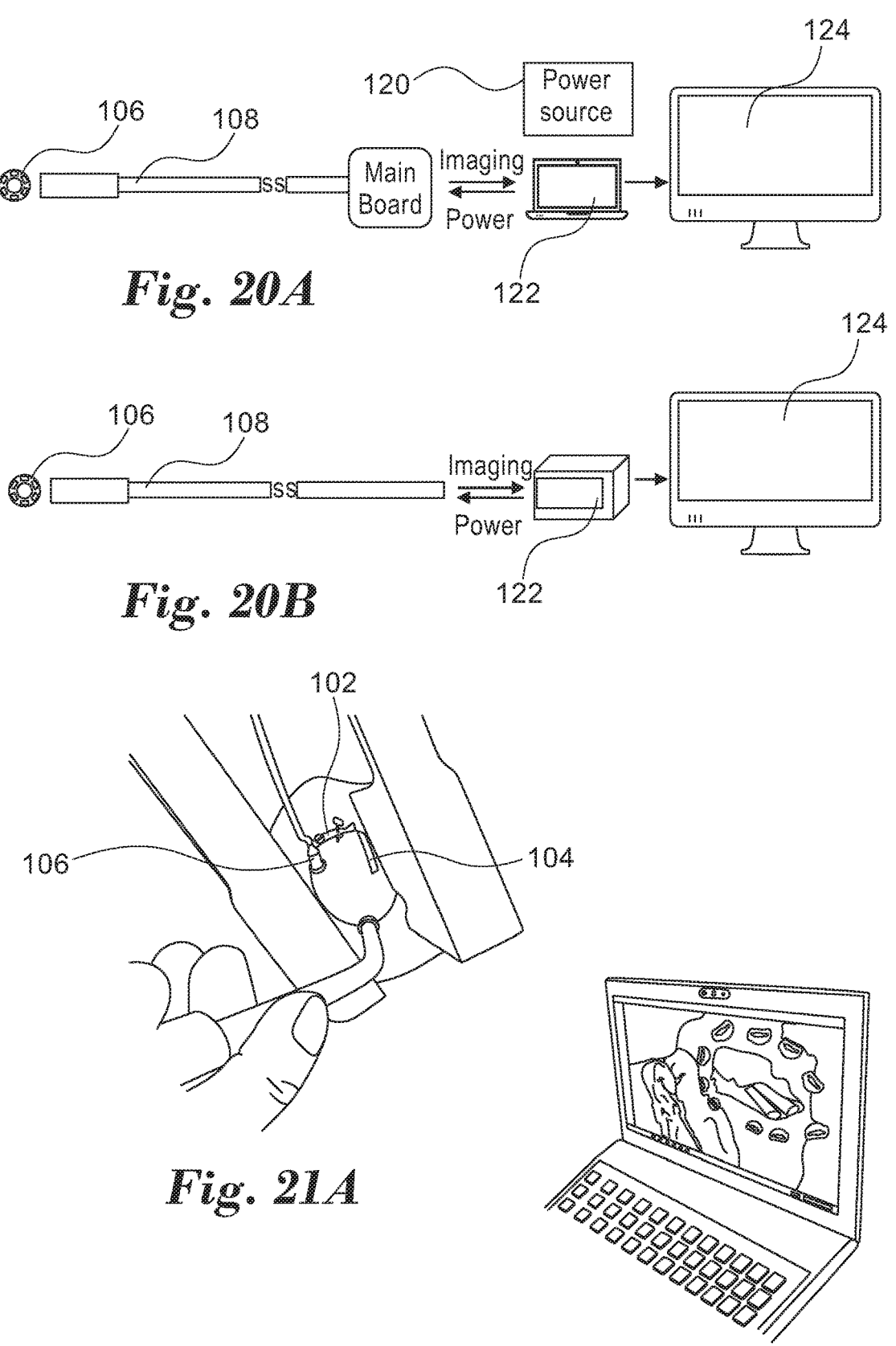
Figure 22C:
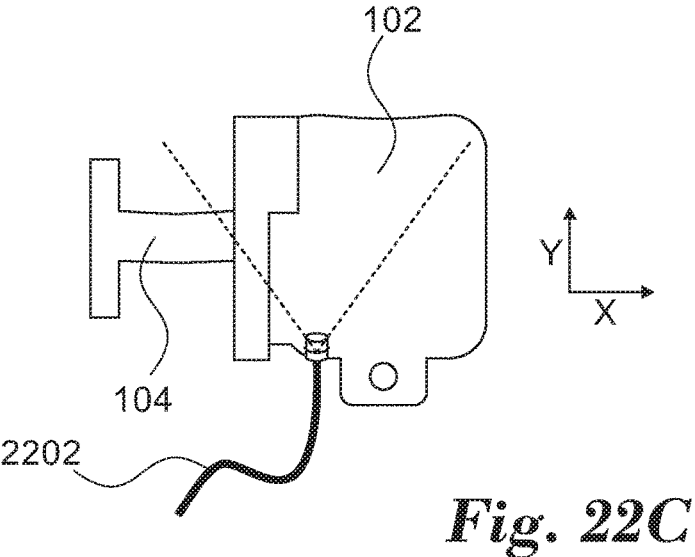

FIG. 4B is a schematic illustration of a top view of an atrium lift retractor with an integrated endoscopic micro-camera, in accordance with embodiments of the present disclosure;

FIG. 4C is a schematic illustration of a bottom view of an atrium lift retractor with an integrated endoscopic micro-camera, in accordance with embodiments of the present disclosure;

FIG. 4D is a schematic illustration of a side view of an atrium lift retractor with an integrated endoscopic micro-camera, whereby the cable passes through the retractor handle, in accordance with embodiments of the present disclosure;

FIG. 4E is a schematic back view illustration of an atrium lift retractor with an integrated endoscopic micro-camera, which cable passes through the retractor incision, in accordance with embodiments of the present disclosure;

FIGS. 5A and 5B are schematic illustrations of a first alternative method of fixating a camera to a camera holding structure, in accordance with embodiments of the present disclosure;

FIGS. 6A and 6B are schematic illustrations of a second alternative method of fixating camera to camera holding structure, in accordance with embodiments of the present disclosure, in accordance with embodiments of the present disclosure;

FIG. 7 is a schematic illustration of a top view of the two-blade atrium lift retractor, in accordance with embodiments of the present disclosure;

FIG. 8A is a schematic illustration of a first alternative side blade of the two-blade atrium lift retractor, in accordance with embodiments of the present disclosure;

FIGS. 8B and 8C are schematic illustrations of a second alternative side blade and a third alternative side blade of the two-blade atrium lift retractor, respectively, in accordance with embodiments of the present disclosure;

FIG. 9 is a schematic illustration of the two blades connected by a torque adjustable hinge, in accordance with embodiments of the present disclosure;

FIGS. 10A to 10C are schematic illustrations of a simple screw connection to connect handle to top blade; in accordance with embodiments of the present disclosure;

FIG. 11 is a schematic illustration of a retractor handle with an inner hollow channel for passing the miniature-video camera therethrough, in accordance with embodiments of the present disclosure;

FIGS. 12A and 12B are schematic illustrations of a first type of camera holder by a swivel ball joint, in accordance with embodiments of the present disclosure;

FIG. 13A is a schematic illustration of a second type of a camera holder by a swivel ball joint positioned inside a grooved edge of the top blade, in accordance with embodiments of the present disclosure;

FIG. 13B is a schematic illustration of a front view of a two-blade atrium lift retractor in "opened" position, with the second type of camera holder, in accordance with embodiments of the present disclosure;

FIGS. 14A to 14F are schematic illustrations of a third type of camera holder, which attaches to the retractor by attraction between magnets, or between magnet to magnetic material, in accordance with embodiments of the present disclosure;

FIGS. 15A and 15B are images of a magnet being coated or embedded, in accordance with embodiments of the present disclosure;

FIGS. 16A and 16B are schematic illustrations of a front view and perspective view, respectively, of a fourth type of camera holder by slide and lock grip/clamp mechanism, in accordance with embodiments of the present disclosure;

FIG. 17A is a schematic illustration of a top view of a three-blade atrium lift retractor, in accordance with embodiments of the present disclosure;

FIGS. 17B and 17C are schematic illustrations of a three-blade retractor in "closed" and "opened" position, respectively, in accordance with embodiments of the present disclosure;

FIG. 18 is a schematic illustration of a four-blade retractor including a single used sheet plate added to a three-blade retractor by sliding into the slots of the two side blades, in accordance with embodiments of the present disclosure;

FIG. 19 is a schematic illustration of a single blade sheet plate added to a three-blade retractor by button/unbutton mechanism, in accordance with embodiments of the present disclosure;

FIGS. 20A and 20B are schematic illustrations of two types of retractor-camera kits, in accordance with embodiments of the present disclosure;

FIGS. 21A and 21B are images of a prototype of a two-blade retractor kit as shown in FIG. 3 and FIG. 4 being used in animal trial for minimally invasive mitral valve surgery (MiMVS), and displayed in a display system, respectively, in accordance with embodiments of the present disclosure; and FIGS. 22A to 22C are schematic illustrations of front and bottom views of retractor-camera kits comprising illumination sources of various types and locations along the retractor, in accordance with embodiments of the present disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present disclosure provide a retractor-camera kit for optimal exposure and visualization of the mitral valve during heart surgery, namely minimally invasive mitral valve surgery (MiMVS) through right minithoracotomy (RT). The retractor-camera kit may comprise an atrium lift retractor comprising a flexible miniature-video camera integrated with a retractor blade at the proximal bottom end of the blade for viewing the surgical field, and further comprising two channels; one channel for at least one light source and a second channel for providing power to the miniature-video camera. However, in some embodiments, the miniature video-camera may be autonomous, thus no external cables may be necessary for providing power to the camera nor for transmitting acquired images from the camera to a display system. The miniature-video camera may comprise a short and solid camera head with CCD or CMOS image sensors along with a flexible long cable connected to the power source and video processor or display. The miniature-video camera may be magnetically mounted onto the retractor blade. The miniature-video camera may come in different sizes, to fit into any sized heart of any patient. The miniature-video camera may also comprise a track or ball-joint into which the camera may slip and click to ensure the miniature-video camera is stabilized to the retractor. The angle of the miniature video camera may be easily adjustable even when attached to the blade, which enables to point the mini-camera at the exact targeted anatomical structure.

According to some embodiments, the retractor-camera kit may comprise an atrium lift retractor integrated with a miniature camera. The atrium lift retractor may be a simple and standard retractor comprising a single retracting blade, a double-blade, triple-blade or even quadruple-blade, that along with the miniature camera improve surgical visualization. Most importantly the retractor may be integrated with a miniature-video camera via a camera holder, which may either be moveable or static by incorporating any of various mechanisms, such as swivel ball joint, magnetic force, or a simple slide and lock grip or clamp.

Figure 1:
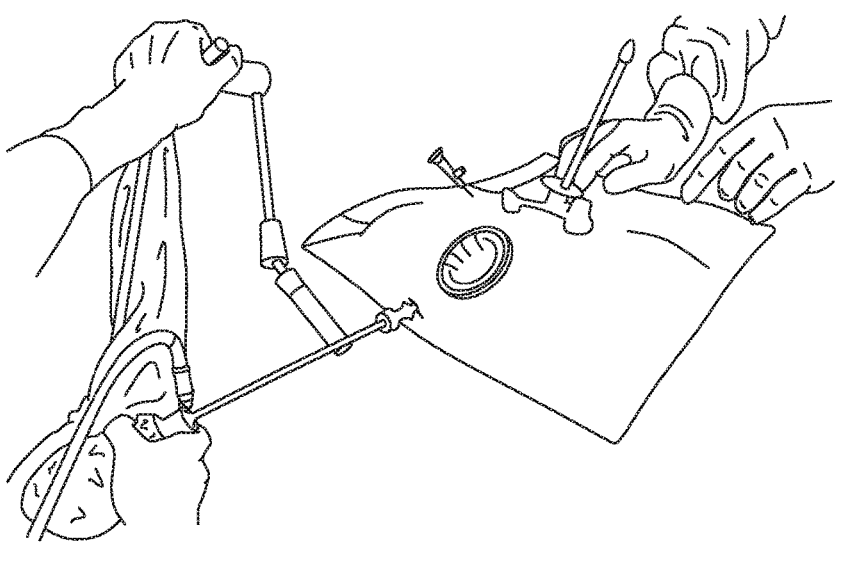
FIG. 1 illustrates an image of a minimally-invasive cardiac surgery, in accordance with prior art.

Reference is now made to FIG. 1, which illustrates an image of a minimally-invasive cardiac surgery, in accordance with prior art. As shown, with current minimally-invasive cardiac surgery, several incisions are made along the chest of the patient going through such surgery, in order to provide ports for imaging, for illumination, and of course ports through which the actual surgical procedure is carried out. It is evident from FIG. 1 that there is a need for a nurse or other surgical assistant to hold the typically stiff and cumbersome endoscopic tube that provides imaging of the surgical site, which consumes a fair amount of space at the surgical site.

Contrary to current minimally-invasive cardiac surgery, the present disclosure provides a retractor-camera kit that may be easily manipulated at the surgical site without requiring any additional incision besides that of the main surgical site, such to reduce patient trauma, bleeding and heart injury risk.

Furthermore, the retractor-camera kit of the present disclosure eliminates the need for an additional staff member at the bedside of the patient, thereby freeing up space at the surgical site for easier maneuverability of the retractor and its integrated camera.

Figure 2:
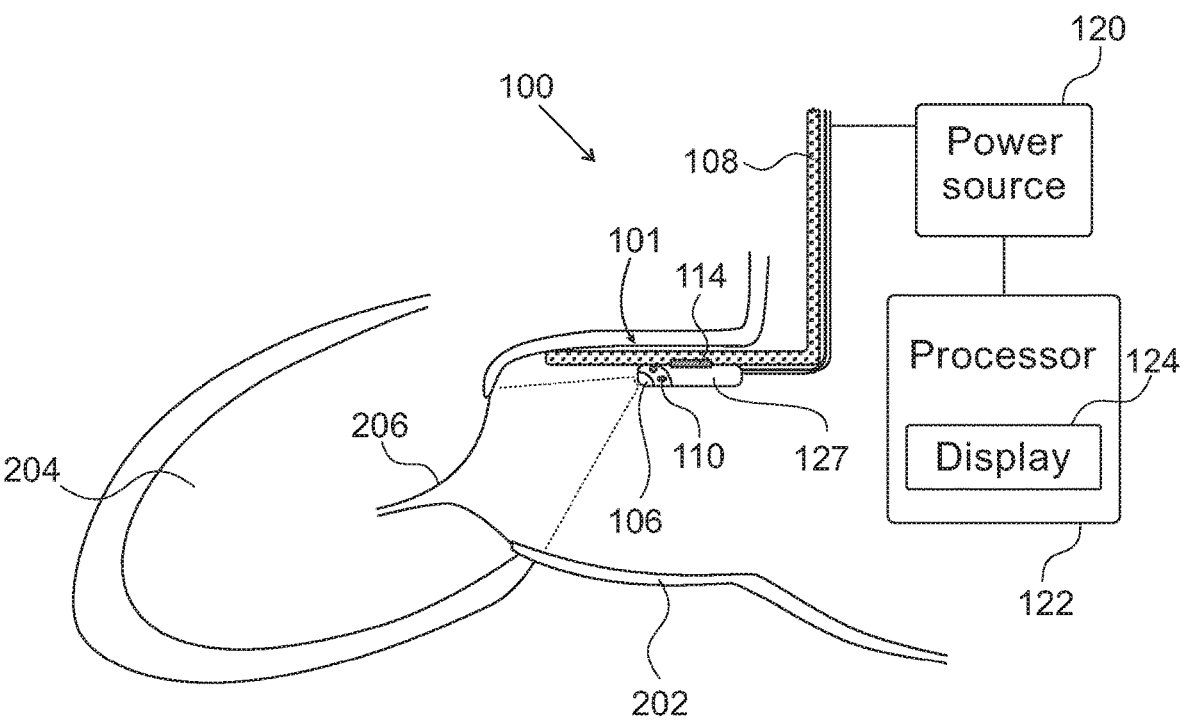
FIG. 2 is a schematic illustration of a side view of an atrium lift retractor-camera kit located in the left atrium, in accordance with embodiments of the present disclosure.

Reference is now made to FIG. 2, which is a schematic illustration of a side view of an atrium lift retractor-camera kit 100 located in the left atrium, in accordance with embodiments of the present disclosure. The retractor-camera kit 100 of the present disclosure may be inserted through an incision in a chest of a patient, for mitral valve surgery. The retractor-camera kit 100 may comprise a camera 106 for capturing images or videos, and a retractor or atrium retractor 101 for expanding the walls of the left atrium 202 (connected to the left ventricle 204) for the camera 106 to have better view of the mitral valve 206. The camera 106 may capture images or videos, and may be an integrated endoscopic micro-camera, a miniature camera, or a miniature video camera. The retractor-camera kit 100 may further comprise a handle 108.

In some embodiments, and as will be explained hereinbelow in detail, the retractor-camera, kit 100 may comprise a retractor top blade 102 with a camera holding structure 114, a camera 106, and possibly illumination sources 110, which may be integrated as part of the retractor 101. In some embodiments, the camera 106 may be connected to a processor 127, whereas in some embodiments, the images acquired by camera 106 may be transferred to an external processor 122, which may further comprise a display unit 124. In addition, camera 106 and illumination sources 110 may be connected to an external power source 120 via cables or wires, or may be wireless of autonomous such to not requires such cables or wires.

Reference is now made to FIG. 3, which is a schematic illustration of a front view of a two-blade atrium lift retractor in a "closed" position integrated with a camera and a holding structure 114 located at a right edge of the top blade 102, in accordance with embodiments of the present disclosure. According to some embodiments, the retractor-camera kit 100 may be introduced into a heart chamber (e.g., the left atrium 202) to lift its wall and generate a direct and broad view of the target surgical site, the mitral valve for mitral valve surgery. In some embodiments, retractor-camera kit 100 may comprise a retractor or atrium retractor 101 comprising two blades, top blade 102 and side blade 104, though other numbers of blades in other configurations may be implemented, as will be described later on. In some embodiments, the top blade 102 may have a concavo-convex shaped surface to fit the upper part of the left atrium. In some embodiments, retractor-camera kit 100 may comprise camera 106, which may be attached to either one of the retractor blades, e.g., top blade 102 or side blade 104 to provide visibility of the surgical site for the surgeon and the operational team. In some embodiments, camera 106 may also provide additional light for better vision by incorporating at least one illumination source 110. In some embodiments, illumination source 110 may be several, e.g., six, high power LED light sources affixed around the camera 106. In some embodiments, a hand-controller of the illumination intensity may be built-in along with the camera cable. In other embodiments, illumination sources 110 may be located at other locations along retractor-camera kit 100 independently of the miniature camera 106.

In some embodiments, retractor-camera kit 100 may comprise a handle or shaft 108 connected to retractor 101 via connecting means located in port 118. Port 118 may be located at any location on retractor 101. In some embodiments, port 118 may be located on a surface of top blade 102. Handle 108 may be screwed into top blade 102 after the retractor 101 is inserted through the chest incision, in order to fixate the retractor 101. Port 118 may comprise a screw thread, while the proximal end of handle 108 may comprise a screw that may be screwed into the screw thread of port 118. Other connecting mechanisms may be implemented. Handle 108 may further be used to change the location of retractor 101 inside the left atrium, in approximately 60 degrees.

In some embodiments, retractor-camera kit 100 may comprise an adjustable hinge 112 located between top blade 102 and side blade 104, which may enable switching between "opened" and "closed" modes of the retractor's blades.

As illustrated in FIG. 3, top blade 102 and side blade 104 are in folded position or "closed" mode. The folded position or "closed" mode is typically required to occupy as little space as possible before and during insertion of the retractor-camera kit 100 through the incision and into the surgical site, for ease of insertion. Folded or "closed" state or mode provides for ease of insertion of the retractor-camera kit 100 into the surgical area, e.g., near the mitral valve.

Figure 4A:
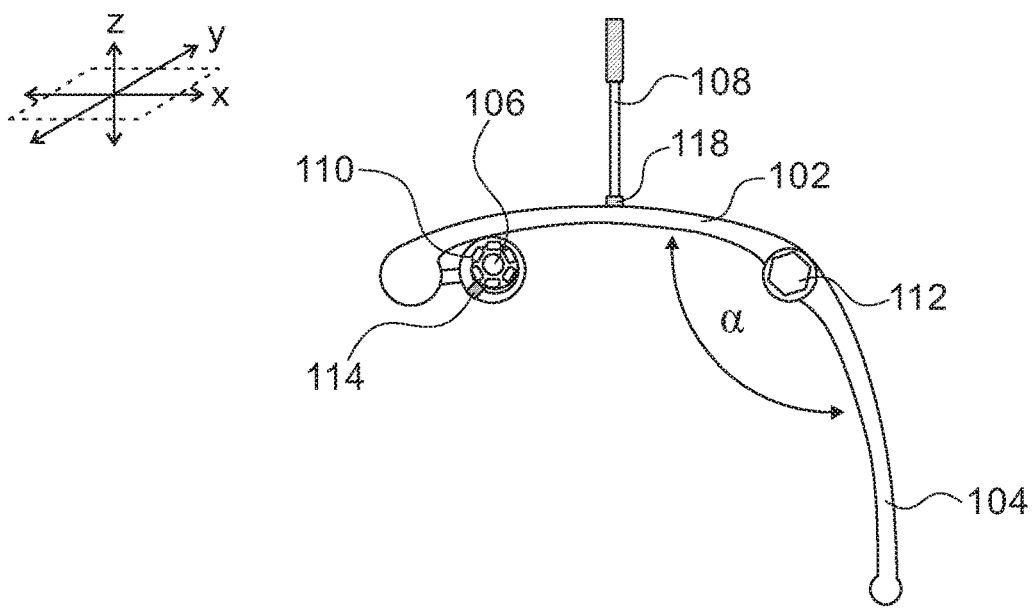
FIG. 4A is a schematic illustration of a front view of a two-blade atrium lift retractor in "opened" position integrated with a camera and a holding structure located at the right edge of the top blade, in accordance with embodiments of the present disclosure.

In some embodiments, and as illustrated in FIG. 4A, side blade 104 may be moved around hinge 112 to distance itself from top blade 102, thereby to open at a degree up to 180 degrees between side blade 104 and top blade 102. Side blade 104 may be opened to any α degree from 0 degrees to 180 degrees with decent holding torque, which may be adjusted by tightening a bolt of hinge 112 with any type of drive, e.g., a hex drive as illustrated in FIG. 9 and detailed hereinbelow. Tightening hinge 112 to maintain the desired opening angle α between top blade 102 and side blade 104 may be done manually. The opening angle α may be adjusted according to patient anatomy, i.e., the size of the left atrium, and fixated by tightening hinge 112.

As illustrated in FIGS. 2 to 4A, according to some embodiments, camera 106 may be mounted on the upper left proximal end of retractor top blade 102. In some embodiments, a mounting or holding structure 114 is secured to the retractor top blade 102. In some embodiments, camera holding structure 114 may be secured to the upper left end of the top blade 102. The miniature camera 106 may preferably have a short rigid camera head that may be configured to be fitted with mounting structure 114. In some embodiments, holding structure 114 may be rotatable at a range of approximately 150 degrees, such that once camera 106 is connected to it, camera 106 may be rotated to change its viewing angles. The camera 106 may be wireless and autonomous or it may comprise a flexible long cable, which may be easily managed and passed through the working incision or working port that leads to the surgical site, while being connected to a power source 120 and possibly a video processor 122, which may comprise a display system 124, for example, a monitor (e.g., HDMI monitor). According to some embodiments, camera 106 may provide both a view of the entirety of the surgical area, e.g., the mitral valve, as well as close-up and magnified images of the area of interest, through customizing the camera parameters such as depth of field, focusing length, field of view or view angle, etc. In some embodiments, processor 122 may be configured to process the images or video images acquired by camera 106 prior to displaying them onto display system 124. Processing of the images may comprise improving quality of the images, though other processing may be performed by processor 122.

Reference is now made to FIGS. 4B to 4D, which are schematic illustrations of a top view, bottom view and side view of an atrium lift retractor with an integrated endoscopic micro-camera, in accordance with embodiments of the present disclosure. In some embodiments, handle 108 may be connected to port 118, which is located as part of top blade 102. Typically, handle 108 may be screwed into port 118, though other connecting method may be implemented to connect the handle 108 to top blade 102 via port 118. As mentioned hereinabove, handle 108 may be connected to retractor 101, and specifically to top blade 102 after the atrium retractor 101 is inserted through the chest incision such to be placed in close proximity to the mitral valve. Once retractor 101 is located at the surgical area, handle 108 may be connected to it such to fixate it in position. In case camera 106 comprises a cable to provide power and or transfer acquired images to a processor and a display unit, the cable 130 may pass through a shaft located along handle 108 and exit through an opening 200 along handle 108 into a camera port, which may be part of camera holding structure 114.

FIG. 4E illustrates a camera comprising a cable 130 which is not passed through handle 108 but is rather passed through the same incision through which retractor 101 is passed through.

In some embodiments, in order to fixate the camera 106 to camera holding structure 114, a screw pin 134 may be screwed towards camera 106 after it is passed through the camera port in camera holding structure 114.

FIGS. 5A and 5B are schematic illustrations of a first alternative method of fixating camera 106 to camera holding structure 114, in accordance with embodiments of the present disclosure. In some embodiments, camera holding structure 114 may be shaped as a block 113 comprising a hole 115 to hold camera 106, the hole 115 located distal from where block 113 connects to retractor 101. In some embodiments, block 113 may have a length of 10.00 mm and a width of 6.00 mm. Preferably, block 113 is made of a stiff material which is still slightly deformable when force is applied such as Polyacetals, Delrin, Acetal Plastic, Nylon plastic, etc. In some embodiments, hole 115 may be shaped as an unenclosed circle with a mouth 116, mouth 116 located at an edge of block 113 for insertion of camera 106 through a side of camera 106 at mouth 116. In sonic embodiments, hole 115 may be shaped as a major segment of a circle with an intercepted arc greater than a semi-circle and with mouth 116 located at the chord of the major segment. In some embodiments, the intercepted arc of hole 115 has a central angle of between 40 and 160 degrees, and preferably 120 degrees. In some embodiments, hole 115 may have a diameter that is slightly narrower than the diameter of camera 106, and preferably between 5 and 15% narrower than the diameter of camera 106 so that camera 106 may be securely held within hole 115 without the need for additional components to secure camera 106 to block 113 as mouth 116 allows hole 115 to expand or open slightly to accommodate camera 106 (see FIG. 5B). It is advantageous to have as little components as possible to reduce the chances of components dropping into the patient's body. In some embodiments, hole 115 may have a diameter of 3.95 mm and mouth 116 may be 3.50 mm wide to hold camera 106 with a diameter 4 mm. In some embodiments, hole 115 may further comprise a slot 117, the slot 117 positioned opposite to mouth 116 to assist mouth 116 to widen when force is applied at mouth 116.

FIGS. 6A and 6B are schematic illustrations of a second alternative method of fixating camera 106 to camera holding structure 114, in accordance with embodiments of the present disclosure, in accordance with embodiments of the present disclosure. In some embodiments, camera holding structure 114 may comprise a hollow structure 119 with a hole 121, the hole 121 comprising a split ring 123 with an opening 125. Hollow structure 119 may be made of a stiff and hard material such as stainless steel. Split ring 123 may be made of a stiff material which is still slightly deformable when force is applied such as Polyacetals, Delrin, Acetal Plastic, Nylon plastic, etc. In some embodiments, split ring 123 may have a width of between 1 and 3 mm. In some embodiments, split ring 123 may have an inner concentric circle with a diameter that is slightly narrower than the diameter of camera 106, and preferably between 5 and 10% narrower than the diameter of camera 106, and an outer concentric circle with a diameter that is the same as or slightly narrower than the diameter of hole 121, and preferably between 0 and 5% narrower than the diameter of hole 121, so that camera 106 may be securely held within split ring 121 without the need for additional components to secure camera 106 to second alternative camera holding structure 114a as opening 125 allows the inner concentric circle of split ring 123 to expand slightly to accommodate camera 106 and allows the outer concentric circle of split ring 123 to expand slightly such that split ring 123 is pressed securely against the inner surface of hole 121 (see FIG. 6B). In some embodiments, hollow structure 119 for a camera 106 with diameter 4 mm may have a hole 121 of diameter 6 mm, a split ring 123 with an inner concentric circle of diameter 4 mm and an outer concentric circle of diameter 5 mm, and an opening 125 with a width of 1 mm.

Reference is now made to FIG. 7, which is a schematic illustration of a top view of the two-blade atrium lift retractor, in accordance with embodiments of the present disclosure. In some embodiments, both top blade 102 and side blade 104 may be strong solid pieces of blades. Having side blade 104 as a solid piece of blade allows efficient pushing of the atrial fold and atrial wall as compared to the U-shaped blade of prior retractors. Prior retractors with a "U"-shaped side blade permit redundant, hypertrophic atrial wall tissue to prolapse between the opening in the U-shaped side blade, which obstructs vision. In some embodiments and as illustrated in FIG. 7, top blade 102 may be a strong solid piece of blade, whereas side blade 104 may be of a "T" shape laid sideways connected to a long vertical leg that is connected to top blade 102 via hinge 112 (FIG. 3) to push the atrial fold and atrial wall more efficiently to provide a clearer view. The stem of "T" shape laid sideways allows also allows efficient pushing of the atrial fold and atrial wall as compared to the "U"-shaped blade of prior retractors by preventing redundant, hypotrophic atrial wall tissue prolapse. The "T" shape is also less traumatic for atrial fold retraction. Since the left atrium shows a fold on its basal wall when retracted from its roof, a "T"-shaped side blade, which would encompass the fold in the middle, is easier to retract with little to no trauma to the left atrial fold. In some embodiments, the dimensions of blades 102 and 104 may vary to accommodate to the variance in the size of the anatomy of the target region, e.g., the mitral valve, per various patients. According to some embodiments, the length of the "T" head 105 of blade 104 may vary between two thirds up to a full length of the top blade 102. In some embodiments, the length of top blade 102 may be 40 mm, the length of the "T" head 105 may be 30 mm, and the length of the "T" leg 107 may be 17.7 mm (with an 8 mm width). In some embodiments, the "T"-shaped side blade 104 may be located at the center of top blade 102 to lift the atrial wall for optimal viewing.

In some embodiments, "T"-shaped side blade 104 may have a higher hinge torque and better control at hinge 112 compared to an "L"-shaped side blade. According to some embodiments, retractor-camera kit 100 may further comprise a blade grasper (not shown) that is configured to assist in positioning the retractor 101 inside the left atrium.

FIG. 8A is a schematic illustration of a third alternative side blade 104a of the two-blade atrium lift retractor, in accordance with embodiments of the present disclosure. In some embodiments, first alternative side blade 104a may be a solid blade with an opening 802 located at a bottom end of first alternative side blade 104a. Opening 802 may extend up to 30% of the length of first alternative side blade 104a, and preferably between 15 and 20%.

FIGS. 8B and 8C are schematic illustrations of a second alternative side blade 104b and a third alternative side blade 104c of the two-blade atrium lift retractor, respectively, in accordance with embodiments of the present disclosure. In some embodiments, side blade 104 may be of a "H" shape comprising a left stem 804, a cross bar 808 and a right stem

812, with the left stem 804 connected to top blade 102. In some embodiments, and as illustrated in second alternative side blade 104b left stem 804 above cross bar 808 of the "H"-shaped side blade 104b may have a width that is wider than left stem 804 below cross bar 808 of the "H" shape (see FIG. 8B). In other embodiments, and as illustrated in third alternative side blade 104c, right stem 812 above cross bar 808 of the "H"-shaped side blade 104c may have a width that is wider than right stem 812 below cross bar 808 of the "H" shape (see FIG. 8C). The wider widths of the top of stems 804 and 812 allow more efficient pushing of the left atrial wall. Similar to the "T" shape previously discussed, the "H" shape also allows efficient pushing of the atrial fold and atrial wall as compared to the U-shaped blade of prior retractors by preventing redundant, hypotrophic atrial wall tissue prolapse.

FIGS. 10A to 10C are schematic illustrations of a simple screw connection to connect handle 108 to top blade 102, in accordance with embodiments of the present disclosure. In some embodiments, handle 108 may connect to top blade 102. In sonic embodiments, handle 108 may comprise a non-through female screw in its proximal end to connect with the retractor's top blade 102, as shown in FIGS. 10A to 10C. A top view of the lower half of the top retractor blade 102 is illustrated in FIG. 10A. The circle indicates the connection point between the handle 108 and top blade 102. i.e., port 118. In some embodiments, a joint may be formed by a female screw with a degree of freedom that may be rotating itself from side to side for up to 60 degrees. The rectangle element illustrated in FIG. 10B is a cross section of the top retractor blade port 118 showing the screw mechanism therein. Handle 108 is illustrated with a screw at its proximal end in FIG. 10C.

According to some embodiments, instead of a screwing mechanism used to connect handle 108 to top blade 102 via port 118, other mechanisms may be implemented, e.g., a socket cap screw, a hex jam nut, a drop-in anchor or a bayonet.

Reference is now made to FIG. 11, which is a schematic illustration of a retractor handle, e.g., handle 108, comprising an inner hollow channel for passing the ultra mini video camera therethrough, in accordance with embodiments of the present disclosure. In some embodiments, retractor handle 108 may comprise a distal end 1101 configured to be easily gripped by a user, which may be connected to a shaft 1102, which may comprise an inner hollow channel 1108 which allows the miniature-video camera, e.g., miniature camera 106 to pass therethrough and ramp out front a flattened elliptical shape opening 1110 at the proximal end in order to be fitted to a camera holding structure as holding structure 114 illustrated in FIG. 3, holding structure 1414 illustrated in FIGS. 14A-14F and holding structure 1614 in FIGS. 16A and 16B. Opening 1110 (FIG. 11) may be located between 2 and 5 mm, and preferably 3 mm, from the proximal end of retractor handle 108. In some embodiments, the mini video camera may be easily passed through the hollow structure of the retractor handle 108 and may be slipped out from opening 1110 near the retractor blades, e.g., blades 102 and 104 (FIG. 2) with less obstruction around the main incision area during a minimally invasive surgery as compared to current imaging systems.

In some embodiments, shaft 1102 of retractor handle 108 may preferably be of tubular shape, though in other embodiments, shaft 1102 may comprise a chamfered surface in order for shaft 1102 to be easily gripped by clamping tools.

In some embodiments, at the proximal end of handle 108 there may be a connection means 1112 for connecting handle 108 to top blade 102 via port 118 (FIG. 4B).

Reference is now made to FIGS. 12A and 12B, which are schematic illustrations of a first type of camera holder 1214 by a swivel ball joint, in accordance with embodiments of the present disclosure. In some embodiments, a swivel hollow ball joint type structure 1216 may be fixed to retractor 101 and a rigid tube head of camera 106 may be inserted into the hollow structure 1216.

Reference is now made to FIGS. 13A and 13B, which are schematic illustrations of a second type of a camera holder 1314 by a swivel ball joint 1316 positioned inside a grooved edge 1318 of the top blade 102 and a front view of a two-blade atrium lift retractor in "opened" position, with the second type of camera holder, in accordance with embodiments of the present disclosure. According to some embodiments, a swivel ball joint 1316 may be secured inside a notch or grooved edge 1318 of the hollow structure of the right rim of top blade 102, while a ring holder 1320 for camera 106 may be connected to the swivel ball joint 1316. Ring holder 1320(1) in FIG. 13A illustrates front and side views of a miniature camera, e.g., camera 106 that is located within the ring holder. Ring holder 1320(2) in FIG. 13A illustrates front and side views of a ring holder without a miniature camera mounted within. Ring holder 1320(3) in FIG. 13B illustrates a side view of a ring holder comprising a miniature camera 106 mounted within, whereby the ring, bolder may rotate along the pivot of swivel ball joint 1316 of camera holder 1314.

In some embodiments, the first type of camera holder 1214 may provide additional viewing angles indicated as 'θ' to the attached camera, e.g., camera 106, compared to the second type of camera holder 1314, while the second type of camera holder 1314 may provide more freedom of movement to the camera, e.g., camera 106, compared to the first type of camera holder 1214. Both types of camera holders 1214 and 1314 may be beneficial especially when camera viewing angle is limited and intervention by a surgeon is required. Accordingly, implementing one of these types of camera holders may eliminate the need for surgeon intervention besides the specific maneuvering of either the viewing angle in holder 1214 or the movement in holder 1314.

In some embodiments, the camera, e.g., camera 106, may be pre-mounted to the retractor 101 before entry into the surgical site or it may be inserted into the camera holding structure (e.g., 114, 1114 or holder 1214) following placement of retractor 101 at the surgical site.

Reference is now made to FIGS. 14A to 14F, which are schematic illustrations of a third type of camera holder, which attaches to the retractor 101 by attraction between magnets, or attraction between a magnet to magnetic material, in accordance with embodiments of the present disclosure. In some embodiments, the field of view of viewing angle of a miniature camera, such as miniature-video camera 106, may be broad enough such that visualization of the entire surgical area is enabled, and thus the structure holding the camera need not require any self-tuning capability. In such embodiments, the miniature-video camera, e.g., camera 106 may be attached to the bottom part of retractor top blade 102, as illustrated in FIGS. 14A and 14B. FIGS. 14A to 14F illustrate an anchoring mechanism operated by magnetic force, in accordance with embodiments of the present disclosure. In some embodiments, a thin plate of magnet or magnetic material 1434 may be embedded within the bottom part of the top retractor blade 102 (FIG. 14A), while the camera holder 1414 may comprise a corresponding magnet or magnetic material 1424 embedded or welded thereon. In some embodiments, magnet or magnetic material 1434 that is embedded in top blade 102 may attract magnet or magnetic material 1424 of camera holder 1414, thereby causing camera 106 that is connected to camera holder 1414 to be anchored to retractor 101 via the attracted magnets or magnetic materials 1424 and 1434 positioned therebetween.

As illustrated in FIG. 14C, top retractor blade 102 may comprise a magnet 1434, while camera holder 1414 comprises magnet 1424; each of the magnets comprising opposing poles—e.g., north and south, whereby opposing poles of magnet 1434 and of magnet 1424 attract one another, thereby connecting camera 106 to retractor 101 via the magnetic connection created between camera holder 1414 and top retractor blade 102.

In some embodiments, the dimensions of magnet plate 1434 embedded within the side of retractor top blade 102 may be extended both horizontally as well as longitudinally along the surface of retractor top blade 102, as illustrated in FIG. 14D. Accordingly, camera 106 may be able to move along both X axis and Y axis, i.e., both horizontally and longitudinally with respect to the surface of retractor 101. When camera 106 is moved along the X axis, it may acquire different views of the surgical site. When camera 106 is moved along the Y axis, it may acquire images with various focusing and magnification of the target being viewed, since movement along Y axis is equivalent to moving closer or further away from the mitral valve. Moving along the Y axis such to get a magnified view of the mitral valve may be required during valve repair.

In some embodiments, as illustrated in FIGS. 14E and 14F, the retractor blades, top blade 102 and side blade 104 (or any additional blade when there are more than two) may be fully made with magnetic material, so that the camera 106 that is held by a structure comprising a magnet (or a magnetic material) may be attached at any position along the retractor blades, thereby assisting the surgical team with viewing and focusing on a larger surgical area of interest. In some embodiments, as illustrated in FIGS. 14E and 14F, instead of one of the retractor blades, typically top blade 102 to comprise a magnetic plate, the entirety of the blades may be made with a magnetic material, e.g., stainless steel. Since camera holder 1414 may comprise a magnet or magnetic plate of its own, the magnet 1424 of camera holder 1414 may be attracted to the magnetic material present within the retractor blades, thereby enabling camera 106 that is attached to camera holder 1114 to be anchored to retractor 101.

Reference is now made to FIGS. 15A and 15B, which are images of magnets being coated or embedded within biocompatible material(s), in accordance with embodiments of the present disclosure. According to some embodiments, since retractor-camera kit 100 is inserted into the human body, it is necessary to ensure that the materials of each element of retractor-camera kit 100 is biocompatible. Accordingly, in some embodiments, to make sure that no issue would be raised with respect to any magnet or magnetic material added to retractor-camera kit 100 for anchoring camera 106 to retractor 101, the magnets or magnetic material used may be coated with, embedded or encapsulated within biocompatible material(s). For example, as illustrated in FIG. 15A, magnets of different sizes and shapes may be coated with Polytetrafluoroethylene (PTFE), while FIG. 15B shows a two-blade retractor-camera kit prototype made from medical grade Polyacetal, which magnetic material or a magnet may be embedded within, at top blade body 102.

Reference is now made to FIGS. 16A and 16B, which are schematic illustrations of a front view and perspective view, respectively, of a fourth type of camera holder by a clamp mechanism, in accordance with embodiments of the present disclosure. In some embodiments, camera 106 may be attached to a retractor's blade, typically top blade 102, via a camera holder comprising an anchoring mechanism such as a slide-and-lock mechanism. The slide-and-lock mechanism may comprise of an angled metal bracket (not shown) located on a bottom surface of the top blade 102 with a matching or complementary adapter (not shown) on camera 106 such that the matching or complementary adaptor on camera 106 slides and locks into the angled metal bracket. In other embodiments, camera 106 may be attached to a retractor's blade, typically top blade 102, via a clamp mechanism whereby at least two opposing tracks or holding structures 1614 may be incorporated to the bottom surface of retractor top blade 102, located at a distance between one another. The distance between the opposing tracks 1614 may be dictated by the size or diameter of camera 106. In some embodiments, each track 1614 may comprise a plurality of clamps 1644 located one next to another along track 1614. According to some embodiments, camera 106 may be slid along the space between the at least two opposing tracks or holding structures 1614 and may then be clamped by the plurality of clamps 1644 after insertion of camera 106 to such camera holder mechanism. In some embodiments, each track 1614 may allow slight shifting of camera 106 along the space between tracks 1614, so that the focusing and magnification of the surgical site being viewed by camera 106 may be fine-tuned.

Reference is now made to FIG. 17A, which is a schematic illustration of a top view of a three-blade atrium lift retractor 1700, in accordance with embodiments of the present disclosure. For the embodiments illustrated in FIGS. 14A to 14F and in FIGS. 16A and 16B, the camera holding structures do not reside at the upper left corner of the top blade 102 as shown in FIG. 3, the latter providing sufficient field of view for camera 106 when retractor 101 is in open state. Thus, to provide proper field of view for camera 106 per the embodiments of FIGS. 14A to 14F and FIGS. 16A and 16B, a third blade 1706 may be able to attach to the surgical kit, connected to top blade 102 on a side opposite the side of top blade 102 that side blade 104 is connected at. The purpose of adding a third blade 1706 is to lift the atrial wall away from the other side of top blade 102 (as does side blade 104 from its side) to provide better vision, e.g., larger field of view for camera 106. According to some embodiments, side blade 1706 may be a rigid blade of a "T"-shaped laid sideways, similarly to side blade 104. In other embodiments, side blade 1706 may be a solid blade (not shown), or further comprise an opening, similar to side blade 104a as illustrated in FIG. 8A. In other embodiments, side blade 1706 may be a rigid blade of a "H" shape, similar to side blades 104b or 104c as illustrated in FIGS. 8B and 8C.

Reference is now made to FIGS. 17B and 17C, which are schematic illustrations of a three-blade retractor 1700 in "closed" and "opened" positions, respectively, in accordance with embodiments of the present disclosure. In some embodiments, side blade 1706 may be connected to top blade 102 of three-blade retractor 1700 from a side opposite the side where side blade 104 is located, e.g., side blade 104 may be connected to top blade 102 on its right side, while side blade 1706 may be connected to top blade 102 from the left side of top blade 102. Side blade 1706 may be connected to top blade 102 via a torque adjustable hinge 1708 (FIG. 17C). In some embodiments, the three blades 102, 104 and 1706 may be easily folded to occupy as little space as possible to enable easy insertion of retractor-camera kit 1700 into the incision area (FIG. 17B). In some embodiments, as illustrated in FIG. 17C, side blade 104 may open to create an angle α between side blades 104 and top blade 102, as detailed hereinabove with respect to FIG. 4A, and side blade 1706 may open to create an angle β between side blade 1706 and top blade 102, whereby each of angles α and β may be any angle between a range of 0 to 180 degrees with decent holding torques, adjusted by tightening a bolt 1708, e.g., a sex bolt (FIG. 17C). In some embodiments, each of the two side blades 104 and 1706 may be of different sizes to accommodate variance in size and anatomy of the target region into which these blades are inserted per patient.

Reference is now made to FIG. 18, which is a schematic illustration of a four-blade retractor 1800 including a sheet plate 1802 added to a three-blade retractor by sliding into slots located along the two side blades, in accordance with embodiments of the present disclosure.

Optimal exposure and visualization of the surgical area is of high importance in minimally invasive surgery. Many efforts have been made to expand the left atrium wall along an entire circle. In some embodiments of the present disclosure, to create a retractor-camera kit that may expand in a substantially circular shape such to cause the tissue wall to distant from the camera at all directions and thereby provide efficient and optimal visualization of the target area, an additional blade may be added to a three-blade retractor, such as three-blade retractor 1700. In some embodiments, fourth blade 1802 may be attached on one end to side blade 104 and on its other end to side blade 1706 to create a closed loop semi-circle retractor configured to expand in a circle-like shape such to distance the tissue walls away from camera 106 in substantially all directions besides the direction at which camera 106 is connected onto the retractor itself. In some embodiments, fourth blade 1802 may be of any of various shapes and sizes and may be made from a flexible material(s) such as malleable stainless steel sheet or a biocompatible polymeric sheet, e.g., polycarbonate in order to ease its attachment to side blades 104 and 1706. For example, fourth blade 1802 may be in the shape of a sheet or plate made of a polycarbonate. In some embodiments, fourth blade 1802 may be for single use, though in other embodiments, it may be reusable. During surgery, the surgeon may easily anchor the fourth blade type sheet 1802 to the two side blades 104 and 1706 by simple mechanisms. In some embodiments, fourth blade 1802 may be inserted into a slot located along each of the two side blades 104 and 1706. One end of fourth blade 1802 may be inserted through slot 1820 of side blade 104, while the other end of fourth blade 1802 may be inserted through slot 1830 of side blade 1406. Each of slots 1820 and 1830 may be located at various locations along the end of corresponding side blades 104 and 1706, two examples illustrated in FIG. 18 as slots grooved at the edges of each side blade 1820 and 1830 or slots located on the inner surface of each side blade 1820' and 1830'. The width of each of the slots 1820 and 1830 or 1820' and 1830' may be dictated by the width of fourth blade 1802.

Reference is now made to FIG. 19, which is a schematic illustration of a single blade sheet plate 1802 added to a three-blade retractor by a button/unbutton mechanism, in accordance with embodiments of the present disclosure. In some embodiments, fourth blade 1802 may be attached to each of side blades 104 and 1706 via a button-like mechanism. For example, fourth blade 1802 may comprise at least one indentation 1902 on each of its ends, with each indentation 1902 configured to fit therein a corresponding protruding element 1804, e.g., a button, which is located on each of the side blades 104 and 1706. Thus, to connect fourth blade 1802 to each of side blades 104 and 1706, the surgeon may press the buttons 1804 located onto each of side blades 104 and 1706 into the corresponding indentations 1902 of fourth blade 1802. In some embodiments, it may be that the buttons may be located on the fourth blade 1802, while the corresponding indentations may be located onto each of side blades 104 and 1705.

Reference is now made to FIGS. 20A and 20B, which are schematic illustrations of two types of retractor-camera kits, in accordance with embodiments of the present disclosure. In some embodiments, the miniature-video camera, e.g., camera 106, which is implemented in the various retractor-camera kits of the present disclosure, may be any OEM (Original Equipment Manufacturer) or third-party off-the-shelf products. Preferably, camera 106 may comprise CCD or CMOS image sensors. In some embodiments, the miniature-video camera 106 may comprise a short and solid camera head and a long and flexible cable. For example, camera 106 may be a ⅛" color CMOS 720p LED camera, comprising lens of F4.0 (M2.2*PO.25) 140 degrees (D).

Two typical working logic of camera 106 are shown in FIGS. 20A and 20B. In some embodiments, camera 106 may be passed through a shaft of a retractor, e.g., retractor 101 (FIG. 2) while a camera's cable (e. g., cable 130, FIG. 4D) may be connected to a video processor or a computer 122, which may provide power to the camera for its continuous operation, whereas in some embodiments, a separate power source 120 may be connected to processor 122. In some embodiments, the camera's cable may enable the transfer of images and/or video that are acquired by camera 106 to the processor or computer 122. In some embodiments, the processor or computer 122 may be connected to a display system 124, e.g., a screen or monitor, through which the video or images may be viewed in real-time or substantially real-time in case some processing is performed on the video images prior to being displayed via a display system.

Reference is now made to FIGS. 21A and 21B which are images of a prototype of a two-blade retractor kit as shown in FIGS. 3 and 4A being used in animal trial for minimally invasive mitral valve surgery (MiMVS), and displayed in a display system, respectively, in accordance with embodiments of the present disclosure. An example of a prototype of a retractor-camera kit, similar to that illustrated in FIGS. 3 to 4E, used in an animal acute trial is shown in image FIG. 21A, for a minimally invasive surgery for mitral valve replacement via standardized procedure of minimally invasive mitral valve surgery (MiMVS) through right mini-thoracotomy (RT). In some embodiments, the exposure of the whole mitral valve may be easily achieved by opening the side blade 104 to an angle of approximately 90 degrees. Visualization may be improved by integrating miniature-video camera 106 as part of the prototype and real time video imaging may be broadcasted on a display system, e.g., a laptop screen, as illustrated in FIG. 21B and if available it may further be displayed with a large display such as a HDMI monitor.

Reference is now made to FIGS. 22A to 22C, which are schematic illustrations of front and bottom views of retractor-camera kits comprising illumination sources of various types and locations along the retractor, in accordance with embodiments of the present disclosure. As illustrated in FIGS. 22A to 22C, an atrium retractor kit of the present invention, e.g., retractor-camera kit 100, may comprise illumination sources for providing sufficient lighting at the surgical site.

According to the top illustration of FIG. 22A, an illumination source may be implemented into retractor kits of the present disclosure, as an added elongated shaped light source 2204, which may or may not be an extension of the camera 106. In some embodiments, the elongated bar or rod-shaped illumination source may comprise a cable 2214 that may either pass through the incision in the chest of the patient or may be passed through a hollow shaft along the retractor kit handle. The bottom illustration of FIG. 22B illustrates the light projection of light source 2204. In some embodiments, the elongated shaped light source 2204 may be inserted into a clamp mechanism similar to that illustrated in FIGS. 16A-16B, such clamp mechanism located on retractor top blade 102 or side blade 104.

According to the top illustration of FIG. 22B, which is a bottom view of an example of a retractor kit of the present disclosure, an illumination source may be implemented as part of a retractor kit as a light source panel 2206 that may be built in or attached along the inside surface of the retractor top blade, e.g., top blade 102 (FIG. 3). In some embodiments, the light source panel 2206 may also be located on side blade 104 (not shown). The bottom illustration of FIG. 22C illustrates the light projection of light source panel 2206 when light source panel 2206 is built in or attached along the inside surface of the retractor top blade.

According to FIG. 22C, an illumination source implemented as part of the retractor kits of the present disclosure may be in the form of a flexible fiber optic 2202 projecting light onto the surgical site. Flexible fiber optic 2202 may be configured to pass through a hollow shaft of the retractor handle 108, alongside the cable of miniature camera 106 or it may pass through the incision made in the patient's chest. Flexible fiber optic 2202 may be attached at any position on retractor 101, including at the edges of top blade 102 or side blade 104. In some embodiments, the light sources at the end of fiber optic 2202 may be built-in within the head of camera 106 while the cable of the fiber optic may be passed either through the incision in the chest of a patient or through a hollow shaft passing through the handle of the retractor kit. In some embodiments, the shaft of retractor handle 108 may be a fiber-optic tube, such that it lights up the moment retractor handle 108 is connected to port 118.

In some embodiments, the illumination source may be light elements built within a tunnel on the retractor 101. In some embodiments, the illumination source may be light elements such as bulbs or lamps in-built along hinge 112 of retractor 101. In some embodiments, the illumination source may be configured to light up only when side blade 104 is opened or when retractor 101 is in an "opened" position.

Other implementations of at least one illumination source to be integrated with the various retractor-camera kits of the present disclosure, for providing additional illumination, may be used.

Conjugated terms such as, by way of example, 'a thing property' implies a property of the thing, unless otherwise clearly evident from the context thereof.

In case electrical or electronic equipment is disclosed it is assumed that an appropriate power supply is used for the operation thereof.

The flowchart and block diagrams illustrate architecture, functionality or an operation of possible implementations of systems, and methods according to various embodiments of the present disclosed subject matter. It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or goups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions, and equivalents are not precluded.

The invention claimed is:

1. A retractor-camera kit for minimally invasive heart surgery, comprising:
   a retractor comprising at least a top blade and a first side blade connected to one another through a hinge;
   a handle configured to be connected to the retractor;
   a camera for acquiring images; and
   a holder onto which the camera is connected and thereby held by the retractor to provide visualization of a surgical site,
   wherein the handle comprises a hollow shaft, and the camera includes a portion within the hollow shaft.

2. The retractor-camera kit of claim 1, wherein the handle further comprises an opening disposed at a proximal end of the handle the opening configured to allow the camera to exit through and reach the holder.

3. The retractor-camera kit of claim 1, wherein said holder is configured to enable maneuverability of the camera while still attached to the holder for directing the camera to different orientations.

4. The retractor-camera kit of claim 1, wherein the holder is attached to the top blade via magnetic attraction.

5. The retractor-camera kit of claim 1, wherein each of said holder and said top blade comprises a magnet configured to connect the holder to the retractor via magnetic attraction.

6. The retractor-camera kit of claim 1, wherein the holder is attached to the retractor via a slide-and-lock mechanism.

7. The retractor-camera kit of claim 1, wherein the holder is fixed to an upper left corner of the top blade by a swivel ball joint.

8. The retractor-camera kit of claim 1, wherein the holder comprises a hole to hold the camera.

9. The retractor camera kit of claim 8, wherein the hole is shaped as an unenclosed circle.

10. The retractor camera kit of claim 8, wherein the hole is shaped as a major segment of a circle.

11. The retractor camera kit of claim 1, wherein the holder comprises a split ring with an opening to hold the camera.

12. The retractor-camera of claim 1, wherein said at least top blade and first side blade are configured to transition tween a closed state and an open state, wherein while in the closed stare, the at least top blade and first side blade are folded by little space for ease of insertion into the surgical site, and while in the said open state, the at least top blade and side blade distance from one another to create an angle of 0 to 180 degrees.

13. The retractor camera kit of claim 1, wherein the at least top blade and at least first side blade are solid plates.

14. The retractor-camera kit of claim 13, wherein the solid plate at least first side blade further comprises an opening at a bottom end of the at least first side blade.

15. The retractor-camera kit of claim 1, wherein the at least top blade comprises a solid plate and the at least first side blade is a laid sideways "T" shaped plate.

16. The retractor camera kit of claim 15, wherein the length of the laid sideways "T"-shaped blade is between two thirds up to a full length of the solid plate at least top blade.

17. The retractor-camera kit of claim 15, wherein the laid sideways "T"-shaped first side blade is located at a center of the solid plate at least top blade.

18. The retractor-camera kit of claim 1, wherein the at least top blade comprises a solid plate and the at least first side blade is a "H"-shaped plate.

19. The retractor camera kit of claim 1, wherein said retractor further comprises a second side blade attached to the top blade on a side opposite the side where the first side blade is attached to the top blade.

20. The retractor-camera kit of claim 19, wherein said retractor further comprises a flexible blade attached by a first end to said first side blade and on a second end to said second side blade to form a semi-circle shaped retractor for expanding and distancing tissue walls away from the camera in a substantially circular shape.

21. The retractor-camera kit of claim 1, further comprising at least one illumination source for illuminating the surgical site.

22. The retractor camera kit of claim 21, wherein said least one illumination source is a light panel incorporated within the top blade.

23. The retractor-camera kit of claim 21, wherein said least one illumination source is a bulb or lamp incorporated along the hinge of the retractor.

* * * * *